(12) United States Patent
Takeshita et al.

(10) Patent No.: US 8,846,751 B2
(45) Date of Patent: Sep. 30, 2014

(54) AGENT FOR INHIBITING PRODUCTION OF HEPATITIS C VIRUS AND ITS USE

(75) Inventors: Masahiko Takeshita, Miyakonojo (JP); Hirohito Tsubouchi, Kagoshima (JP); Hirofumi Uto, Kagoshima (JP); Hiroaki Kataoka, Miyazaki (JP); Takanori Kai, Miyazaki (JP); Hideaki Hirabaru, Miyazaki (JP); Miho Sakai, Miyazaki (JP); Ena Akamatsu, Miyazaki (JP)

(73) Assignees: Miyazaki Enterprise Promotion Organization, Miyazaki (JP); Miyazaki Prefecture, Miyazaki (JP); Unkai Shuzo Co., Ltd., Miyazaki (JP); Minami Nippon Dairy Co-Op Co., Ltd., Miyazaki (JP)

( * ) Notice: Subject to any disclaimer, the term of this patent is extended or adjusted under 35 U.S.C. 154(b) by 485 days.

(21) Appl. No.: 13/204,219

(22) Filed: Aug. 5, 2011

(65) Prior Publication Data
US 2011/0288164 A1 Nov. 24, 2011

Related U.S. Application Data

(62) Division of application No. 12/546,281, filed on Aug. 24, 2009, now abandoned.

(30) Foreign Application Priority Data

Sep. 3, 2008 (JP) ................................. 2008-226425

(51) Int. Cl.
*A01N 43/16* (2006.01)
*C07D 311/62* (2006.01)
*A61K 31/74* (2006.01)
*A61K 36/45* (2006.01)

(52) U.S. Cl.
CPC .................. *A61K 31/74* (2013.01); *A61K 36/45* (2013.01); *C07D 311/62* (2013.01)
USPC ............ 514/456; 424/732; 549/415; 549/399

(58) Field of Classification Search
None
See application file for complete search history.

(56) References Cited

U.S. PATENT DOCUMENTS

| 5,211,944 | A | 5/1993 | Tempesta |
| 6,800,433 | B1 | 10/2004 | Honda et al. |
| 2008/0044453 | A1* | 2/2008 | Kobayashi et al. ........... 424/439 |

FOREIGN PATENT DOCUMENTS

| JP | 2003-277271 | | 10/2003 |
| JP | 2005-239581 | | 9/2005 |
| JP | 2006-511509 | | 4/2006 |
| JP | 2007-119398 | * | 5/2007 |
| JP | 2007119398 A | * | 5/2007 |

| WO | 00/64883 | 11/2000 |
| WO | 2004/047847 | 6/2004 |
| WO | 2005/030200 | 4/2005 |

OTHER PUBLICATIONS

Feitelson (Hepatitis C virus: from laboratory to clinic, p. 70 (2002)).*
Nawa (Production of anthocyanins, carotenoids, and proanthocyanidins by cultured cells of rabbiteye blueberry (*Vaccinium ashei* Reade), Biosci. Biotech. Biochem., 57(5), 770 (1993)).*
Tsubouchi (JP 2007-119398 published on May 17, 2007) Machine translation.*
Nawa, et al., Production of anthocyanins, carotenoids, and proanthocyanidins by cultured cells of rabbiteye blueberry (*Vaccinium ashei* reade), Biosci. Biotech. Biochem., 57(5), 770 (1993).*
Feitelson (Hepatitis C virus: from laboratory to clinic, p. 70 (2002).*
Saburo Ito, "Series Shokuhin Kajitsu no Kagaku", Oct. 30, 1991, pp. 60-74, 103-129, 187-204.
Tojiro Tsushida, "Chumoku no Kenkosozai to Kinokenkyu, Blueberry no Seiritekikinosei", Shokuhin to Kaihatsu, vol. 31, No. 3, 1996, pp. 5-8.

(Continued)

Primary Examiner — Robert A Wax
Assistant Examiner — H. Sarah Park
(74) Attorney, Agent, or Firm — Greenblum & Bernstein, P.L.C.

(57) ABSTRACT

This invention provides an agent for inhibiting production of hepatitis C virus with notable anti-HCV activity and without side-effects. The agent comprises a proanthocyanidin polymer composition illustrated in the following the general formula (1), General formula (1)

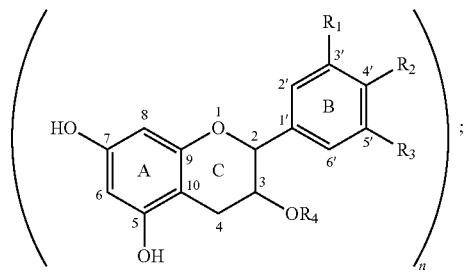

wherein $R_1$ is hydrogen or hydroxyl, $R_2$ is hydroxyl, $R_3$ is hydrogen when $R_1$ is either hydrogen or hydroxyl, but $R_3$ is possibly hydroxyl when $R_1$ is either hydrogen or hydroxyl to the extent that both $R_1$ and $R_3$ being hydroxyl is at most 40 percents in the proanthocyanidin polymer composition said units of flavan-3-ol being bonded each other in any one of three patterns as follows;
(i) a bond between carbon at the position 4 and carbon at the position 8,
(ii) a bond between carbon at the position 4 and carbon at the position 6,
(iii) a bond between carbon at the position 4 and carbon at the position 8, and between carbon, at the position 2 and oxygen at the position 7.

6 Claims, 11 Drawing Sheets

(56) References Cited

OTHER PUBLICATIONS

Office Action that issued with respect to patent family member Japanese Patent Application No. 2008-226425, dated May 17, 2011; along with an english translation thereof.

S. Iino, Medical Digest, vol. 46, No. 6, p. 19-22, 1997, along with a partial English language translation.

N. Sakamoto et al., Japan clinic, vol. 62, p. 116-120, 2004, along with a partial English language translation.

V. Lohmann et al., Science, vol. 285, p. 110-113, 1999.

H. Sakamoto et al., Nat. Chem. Biol., vol. 1, No. 6, p. 333-337, 2005.

N. Krieger et al., J. Virol., vol. 75, No. 10, p. 4614-24, 2001.

L. Porter et al., Phytochem., vol. 25, No. 1, p. 223-230, 1986.

T. Shoji et al., J. Agric. Food Chem., vol. 54, No. 3, p. 884-892, 2006.

S. Guyot et al., J. Agric. Food Chem., vol. 49, No. 1, p. 14-20, 2001.

R.S. Thompson et al., J. Chem. Soc. Perkin Trans. 1, p. 1387-1399, 1972.

L.Y. Foo et al., J. Nat. Prod., vol. 63, No. 9, 1225-1228, 2000.

L. Gu et al., J. Agric. Food Chem., vol. 50, No. 17, p. 4852-4860, 2002.

Prodrugs, Modern Pharmaceutics 596 (Banker et al. eds.) (3d ed. 1996).

Wermuth, Similarity in Drugs: Reflection on Analogue Design, 11 Drug Discovery Today 348-54 (2006).

Fukuchi et al. (Inhibition of herpes simplex virus infection by tannins and related compounds, Antiviral Res., 11:285-298 (1989).

* cited by examiner

AGENT FOR INHIBITING PRODUCTION OF HEPATITIS C VIRUS AND ITS USE

RELATED APPLICATIONS

The present application is a divisional of U.S. patent application Ser. No. 12/546,281, filed Aug. 24, 2009, which claims priority to Japanese Application No. JP2008-226425, filed Sep. 3, 2008, both of which are hereby incorporated herein by reference in their entirety.

BACKGROUND OF THE INVENTION

1. Field of the Invention

This invention relates to an agent for inhibiting production of hepatitis C virus. In particular, this invention also relates to use of proanthocyanidin.

2. Related Background Art

Hepatitis C virus (hereinafter referred to as HCV) has been found as a major causal virus of non-A non-B hepatic inflammation after blood transfusion. HCV is a single-strand RNA virus having an envelope and belongs to *Hepacivirus* of Flaviviridae.

In some cases, HCV carriers progress directly to chronic hepatitis without acute hepatitis and then to cirrhosis after many years. About 50 percents of HCV carriers go onto the development of hepatocellular carcinoma. It is said that main cause of such development is persistent infection with HCV. The persistent infection tends to occur even in adults who were infected with HCV after establishing immune system. Even in case of a patient whose site or sites of hepatocellular carcinoma has been completely removed by surgery, the patient still remains at high risk of recurrence, result of the persistent infection repeatedly occurred in unremoved sites.

Japanese Patent Application Laid-Open No. 2007-119398 disclosed that the process materials of blueberry leaves are effective for inhibiting production of HCV. The publication has, however, no disclosure as to any effective chemical substance contained in blueberry leaves.

It is reported in Japanese Patent Application Laid-Open No. 2005-239581 that Pycnogenol or proanthocyanidin has anti-virus activities and is useful to improve the quality of life in carriers of HCV. In this publication, the target virus effective of Pycnogenol is myocarditis virus, but it is not HCV. The inhibition of HCV production, which is unlike myocarditis virus, is not able to evaluate by any model animal except chimpanzee. In view of this, there is no explicit description in the publication about the inhibition of HCV production by proanthocyanidin.

WO2004/047847 refers to an antiviral action of proanthocyanidin and suggests that the proanthocyanidin might be usable for treating hepatic inflammation. Nevertheless, the antiviral action in the publication is against West Nile virus of Flaviviridae. Although HCV belongs to same family, it differs from the West Nile virus in taxonomic genus and the site of infection. The publication has no suggestion as to inhibitory activity of proanthocyanidin for production of HCV.

U.S. Pat. No. 5,211,944 disclosed that a proanthocyanidin polymer composition having 2 to 11 flavonoid units is specifically useful for treating respiratory virus infection such as respiratory syncytial virus, influenza virus and parainfluenza virus infection, but the respiratory virus is quite different from HCV. So, the publication dose not drop any hint about possible activity of proanthocyanidin against HCV production.

These days, the interferon therapy is only effective method for inhibiting production or proliferation of HCV, or eliminating HCV. Even so, around 50 percents of the HCV carriers still remain at risk for onset of hepatocellular carcinoma due to failure to clean HCV completely. It is also suggested that interferon should be administered together with ribavirin to enhance disappearance rate of HCV. Further, continuous dosing of interferon in a low dose has been introduced to inhibit progress of hepatitis C disease and then to retard eventually the onset of hepatocellular carcinoma.

In each case, it is unavoidable to leave some patients who cannot receive the continuous interferon therapy for a long period, because of its strong side-effects such as dehairing, decreased appetite, thrombopenia, depression of white blood cell and so on (See; Shiro Iino, *Medical Digest*, vol. 46, no. 6, pp. 19-22, 1997).

An object of this invention is to provide an agent for effectively inhibiting production of HCV with fewer side-effects.

Another object of this invention is to provide an agent for inhibiting onset, progress and treating of hepatic disease arisen from HCV.

Further object of this invention is to provide dietary supplements for inhibiting onset or progress of hepatic disease arisen from HCV.

SUMMARY OF THE INVENTION

We, inventers had already found that blueberry leaves have strong suppressive activity against production or proliferation of HCV (See; Japanese Patent Application Laid-Open No. 2007-119398). At that time, it was unclear what effective chemical substance contained in blueberry leaf is. As a result of continuing research on this matter, we have successfully identified that the proanthocyanidin polymer composition with specific chemical formula contained in blueberry leaves has the strong inhibitory activity of HCV production. And then such a finding has led us to this invention.

An aspect of this invention resides in an agent for inhibiting production of HCV comprising a proanthocyanidin polymer composition. The proanthocyanidin polymer composition has a structure in which flavan-3-ols illustrated in the general formula (1) are bound each other through any of the bond pattern (i), (ii) and (iii) mentioned below. Among the general formula (1), the proportion of flavan-3-ol in which both $R_1$ and $R_3$ are hydroxyl is at most 40 percents.

(i) the bond between carbon at the position 4 and carbon at the position 8
(ii) the bond between carbon at the position 4 and carbon at the position 6
(iii) the bond between carbon at the position 4 and carbon at the position 8, and carbon at the position 2 and oxygen at the position 7

General formula (1)

[Chemical structure of flavan-3-ol with positions labeled: HO at 7, OH at 5, ring A with positions 6, 5, 10, ring C with positions 9, 10, 2, 3, 4 and OR$_4$ at 3, ring B with positions 1', 2', 3', 4', 5', 6', R$_1$ at 3', R$_2$ at 4', R$_3$ at 5', with subscript n]

In the formula (1), $R_1$ is hydrogen or hydroxyl, $R_2$ is hydroxyl, $R_3$ is hydrogen when $R_1$ is either hydrogen or hydroxyl, but $R_3$ is possibly hydroxyl when $R_1$ is either hydrogen or hydroxyl to the extent that both $R_1$ and $R_3$ being hydroxyl is at most 40 percents in the proanthocyanidin polymer composition, and $R_4$ is hydrogen or a univalent organic acid group.

In this invention, the agent for inhibiting HCV production comprising the proanthocyanidin with the structure aforementioned has advantages of fewer side-effects, dosing over a long period of time and effective anti-HCV production activity.

In the agent containing proanthocyanidin, $R_4$ in the general formula (1) is preferably a gallate group allowed to have substituent groups.

Further, in the HCV production inhibitor of this invention, the ratio of the concentration of proanthocyanidin polymer composition inhibiting 50 percents of HCV virus proliferation (IC50) divided by the concentration of proanthocyanidin polymer composition inhibiting 50 percents of cell proliferation (CC50) is desirably at most one tenth. Such an inhibiting agent of HCV production has fewer side-effects and can be dosed for a long period of time.

The HCV production inhibitor of this invention has the structure in which proanthocyanidin polymer composition has preferably flavan-3-ol unit of the general formula (1) bound each other in any one of the bond pattern (i), (ii) or (iii).

Another aspect of this invention resides in an agent or a prodrug for treating the hepatic disease arisen from HCV.

Another aspect of this invention resides in an agent or a prodrug for inhibiting onset or progress of the hepatic disease arisen from HCV.

Further aspect of this invention resides in a dietary supplement including food or drink for inhibiting onset, progress or treating of the hepatic disease arisen from HCV.

According to this invention, the agent for inhibiting production of HCV has advantages of significant anti-HCV activities with fewer side-effects and a long dosing period of time.

The inhibiting agent of HCV production comprising the proanthocyanidin has less cytotoxicity in addition to higher anti-HCV replicon proliferation in vitro. It is, therefore, useful for alternative medicines or dietary supplements instead of interferon. The agent has also advantages to be able to dose continuously for a longer period of time, owing to fewer side-effects compared with interferon. In case of the patients having cirrhosis or hepatocellular carcinoma, numbers of platelets or leucocytes are so small that they would be unable to receive continuously the interferon therapy. The therapy using the agent of this invention can, therefore, become an effective alternative therapy for interferon. The proanthocyanidin is useful for a functional dietary supplement including food or drink as well.

DESCRIPTION OF THE PREFERRED EMBODIMENTS

Figure 1:
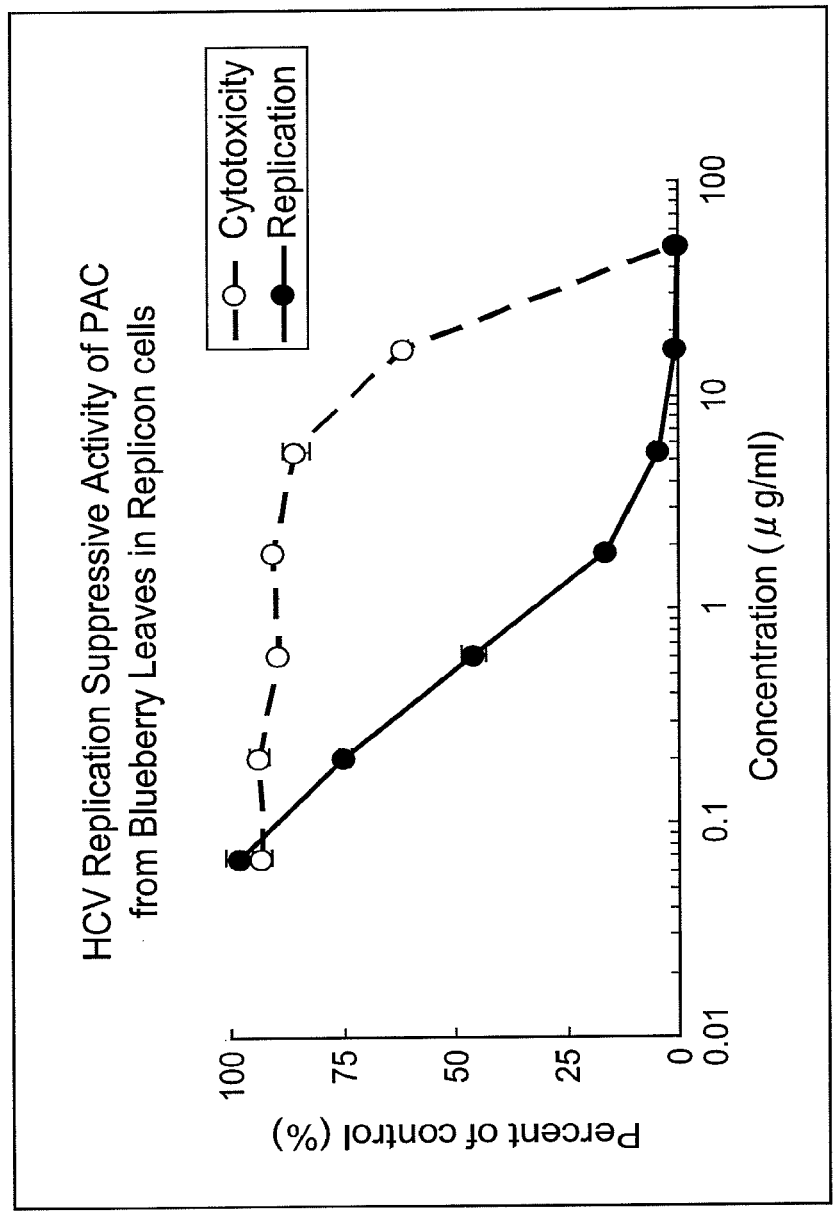
FIG. 1 shows HCV replication suppressive activity of PAC from blueberry leaves in replicon cells.

Referring to the drawings according to need, the preferred embodiments of this invention are described in detail, but does not limit this invention in scope.

The inhibitory agent for production of HCV in this invention comprises a proanthocyanidin polymer composition (herein after referred to as PAC).

The PAC in this invention is a polymer composition of matter wherein the monomer unit in the general formula (1) is combined each other in three bond patterns below. The number of monomer unit defining the polymerization degree of PAC is at least 3, preferably at least 5, more preferably 5 to 10. The typical bond patterns of the monomer unit are described bellow.

(i) the bond between carbon at the position 4 and carbon at the position 6
(ii) the bond between carbon at the position 4 and carbon at the position 8
(iii) the bond between carbon at the position 4 and carbon at the position 6, and carbon at the position 2 and oxygen at the position 7

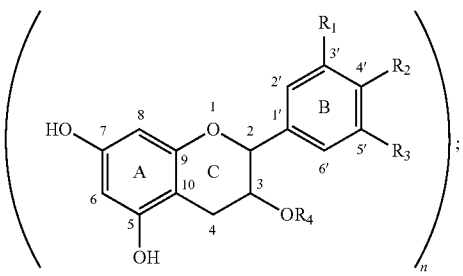

General formula (1)

In this formula (1), $R_1$ is hydrogen or hydroxyl, $R_2$ is hydroxyl, $R_3$ is hydrogen when $R_1$ is either hydrogen or hydroxyl, but $R_3$ is possibly hydroxyl when $R_1$ is either hydrogen or hydroxyl to the extent that both $R_1$ and $R_3$ being hydroxyl is at most 40 percents in the proanthocyanidin polymer composition, and $R_4$ is hydrogen or a univalent organic group respectively.

As the univalent organic group at the position $R_4$, there can be listed a gallate group, an organic acid residue, and a sugar residue. The organic acid may be p-coumarin acid, caffeic acid, ferulic acid, sinapic acid, p-hydroxylbenzoic acid, gallic acid, acetic acid, oxalic acid, malonic acid, succinic acid, malic acid and so on.

$R_4$ may also be glycoside residue in which sugars are bound with organic acid residue or gallate groups. The sugars are bound with a phenolic hydroxyl of the gallate groups or the organic acid groups through ester bonds at any position. For instance, there are hexose residues of pyranose type and pentose residues of furanose type. The sugars may be monosaccharide including glucose, galactose, rhamnose, xylose and arabinose, and either disaccharide or trisaccharide.

Among them, $R_4$ is preferably a gallate group permitted to have substituent groups consisting of a gallate group or a gallate group with substituent. The gallate group with substituent includes a gallate group with which sugar are bound.

Further, each hydroxyl of A-ring at the position 5 and for the position 7 may be replaced by modified groups such as a gallate group, sugar, organic acid and the like.

Among all flavan-3-ol units forming the PAC polymer composition, the proportion of flavan-3-ol of which both $R_1$ and $R_3$ are hydroxyl is at most 40 percents. In case the proportion is more than 40 percents, it is insufficient to suppress production of HCV. The proportion can be measured by thiol cleavage method.

For example, one of the PAC of this invention cab be illustrated in the general formula (2), wherein flavan-3-ol units are bound each other at the bond pattern (i).

General formula (2)

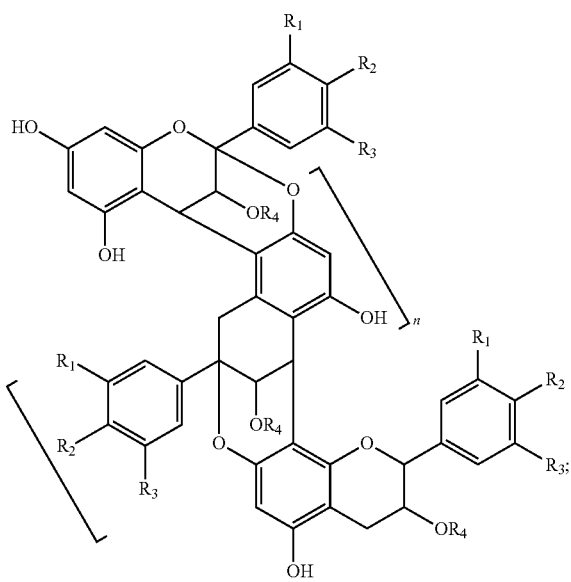

Further, there may be a PAC illustrated in the general formula (3), wherein flavan-3-ol units are bound each other at the bond pattern (iii).

General formula (3)

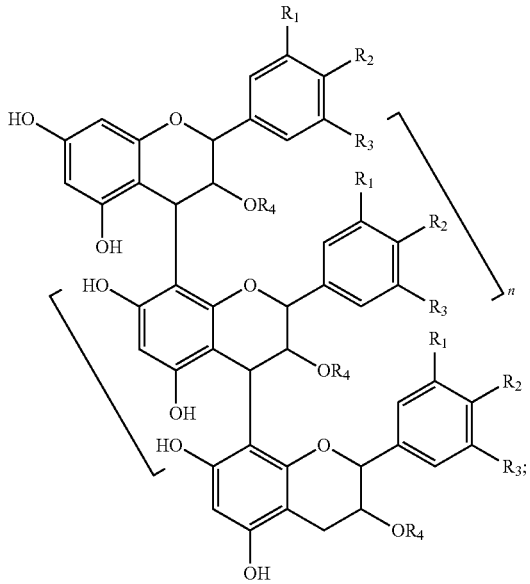

In the general formula (1), $R_1$ and $R_3$ are hydrogen or hydroxyl, $R_2$ is hydroxyl, $R_4$ is oxygen or a univalent organic group, provided that the proportion of both $R_1$ and $R_3$ being hydroxyl is at most 40 percents. Only such a PAC polymer composition can express suppressive activity of the HCV replication in this invention. While the PAC polymer composition wherein the proportion of both $R_1$ and $R_3$ being hydroxyl is more than 40 percents cannot meet the criterion level of the suppressive activity of HCV replication in this invention.

Although the position 5 and/or 7 of A-ring in the monomer unit of the general formula (1) is hydroxyl, at least one of them may be a univalent modified group bound therewith. Typical modified groups may be a gallate group, sugar or organic acid.

In this invention, the anti-HCV production activity is actually an activity for inhibiting the replication of HCV replicon cell in vitro, and can be expressed as anti-HCV production activity value (IC50; µg/ml or the ratio between the anti-HCV production activity value (IC50; µg/ml) and the cytotoxicity value (CC50; µg/ml). It is desirable that the anti-HCV production activity value (IC50; µg/ml) is at most 1.0; µg/ml in terms of the IC50 of interferon. While the ratio of cytotoxicity activity value (CC50; µg/ml) divided by anti-HCV production activity value (IC50; µg/ml) is at least 10 in terms of effectiveness as medicine (See; Naoya Sakamoto et al. *Japan clinic*, vol. 62, p. 116-120, 2004). The effect of PAC in this invention can be evaluated with the ratio.

PAC is a kind of the condensed tannin contained in various plants, and can be treated by acids to give cyanidin, delphinidin, pelargonidin, aurantinidin, luteolinidin, peonidin, malvidin, petunidin, europinidin, rosinidin, hirsutidin, apigeninidin and so on. As illustrated in the general formula (1) and (4), the PAC belongs mainly to catechin class, namely, polyphenol groups consisting of condensation polymer, of which polymerization degree of the flavan-3-ol units is at least 2. In these general formulas, R corresponds to $OR_4$ set forth above. Further, a gallic acid is often bound with hydroxyl at the position 3 of flavan-ring through an ester-link. In other words, PAC can be said to be a generic term including various compositions of matter formed by polymerization of the flavan unit which has hydroxyl at some binding positions. Among the units constituting the polymer, the rear anchor is referred to as 'terminal unit' and the other units 'extension unit'. A polymerization degree of the units extends over the wide range from dimmer to polymers having 100 units or more.

General formula (4)

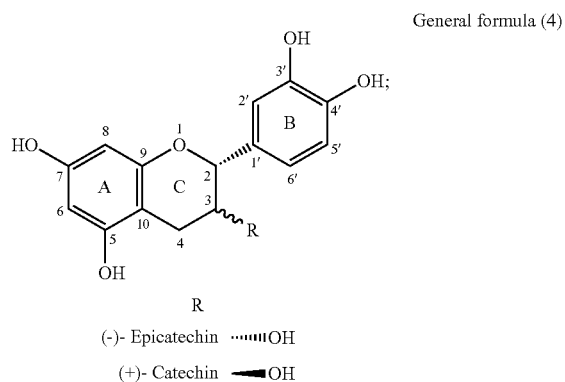

(-)- Epicatechin ·····ıııOH (+)- Catechin ━━OH

Some polymers in which specified monomer is polymerized are called trivial names. The typical trivial names defined or classified depending on numbers of hydroxyl in B-ring of the flavan units are properalgonidin (4'-OH), procyanidin (3'-OH, 4-OH) or prodeiphinidin (3'-OH, 4'-OH, 5'-OH). In addition, there are proguibourtinidin, profisetinidin and prorobinetinidin, all of which has no hydroxyl at position 5 of A-ring of the flavan units. Depending on whether hydroxyl would be at the specific binding position of flavan units, there are given such a trivial name as proteracacidin, promelacacidin, proluteolinidin and so on.

In this invention, the PAC comprises proanthocyanidin, properalgonidin and/or prodelphinidin. The constituent units of procyanidin may be either one or more of same or different groups, and at least one selected from the group consisting of catechin, epicatechin, catechin gallate and epicatechin gallate. The constituent units of prodelphinidin can also be either one or more of same or different groups, and at least one selected from the group consisting of gallocatechin, epigallocatechin, gallocatechin gallate and epigarocatechin gallate.

In case $R_4$ of the PAC in the general formula (1) is residues of the univalent organic acid, such as a gallate group, residue of sugar, residue of organic acid, wherein term 'residue' means a univalent group or groups caused by losing atom or group in the molecular. As the organic acid in the organic acid residues, there are p-coumaric acid, caffeic acid, ferulic acid, sinapic acid, p-hydroxylbenzoic acid, gallic acid, acetic acid, oxalic acid, malonic acid, succinic acid, and malic acid and so on.

Sugar in the sugar residue may be bound with the hydroxyl of phenol in any binding position thereof through an ester bond to modify. For instance, the residues constituting glycoside may be hexose residue of pyranose form and pentose residue of furanose form. As concrete example of form of saccharide, there is monosaccharide including glucose, galactose, rhamnose, xylose, arabinose etc., and other disaccharide or trisaccharide.

The main binding positions among units constituting the PAC are (i) (ii) or (iii) set forth above. As practical embodiment, there are A-type bond consisting of both the bond of carbons at the position 4 and 8, and the bond of carbon at the position 2 and oxygen at the position 7, and B-type bond consisting of either the bond of carbons at the position 4 and 6, or bond of carbon at the position 4 and 8. In addition to these, there are various stereoisomeres with the combination of these bond forms.

The PAC as illustrated in the general formula (3) and (4) has A-type bond and B-type bond. According to the findings of the inventers, however, the difference in the extension of A-type bond and B-type bond, or the mixture ratio therebetween does not affect the anti-HCV production activity of the PAC. In the PAC extracted from blueberry, both of the polymerization degree and the proportion of hydroxyl in B-ring in the PAC polymer composition must meet the criterion of this invention, though the B-type bond is dominant.

According to the differences in binding positions on the rings, there are various PAC polymer compositions, such as steric conformation of substituent groups in flavan unit and binding order among a variety of flavan units. The chemical names of the PAC in this invention are listed as follows. The letters in parentheses express chemical formula. This invention may encompass PACs of higher polymerization degrees, which are polycondensated with constituent units such as catechin and epicatechin, or with other proanthocyanidin.

Proanthocyanidin PZ 5 (C75 H62 O31)
Proanthocyanidin BP 1 (Unspecified)
Proanthocyanidin RP 4 (C129 H106 O67)
Proanthocyanidin RP 3 (C136 H120 O70)
Proanthocyanidin CS 4 (C136 H120 O70)
Proanthocyanidin CS 3 (C127 H128 O69)
Proanthocyanidin CS 2 (C113 H110 O62)
Proanthocyanidin CS 1 (C121 H118 O65)
Proanthocyanidin RP 2 (C120 H114 O64)
Proanthocyanidin RP 1 (C125 H130 O69)
Proanthocyanidin T 4 (C128 H122 O65)
Proanthocyanidin T 3 (C105 H102 O59)
Proanthocyanidin T 2 (C67 H54 O29)
Proanthocyanidin T 1 (C87 H72 O43)
Proanthocyanidin C 1 (C45 H38 O18)

Figure 11:
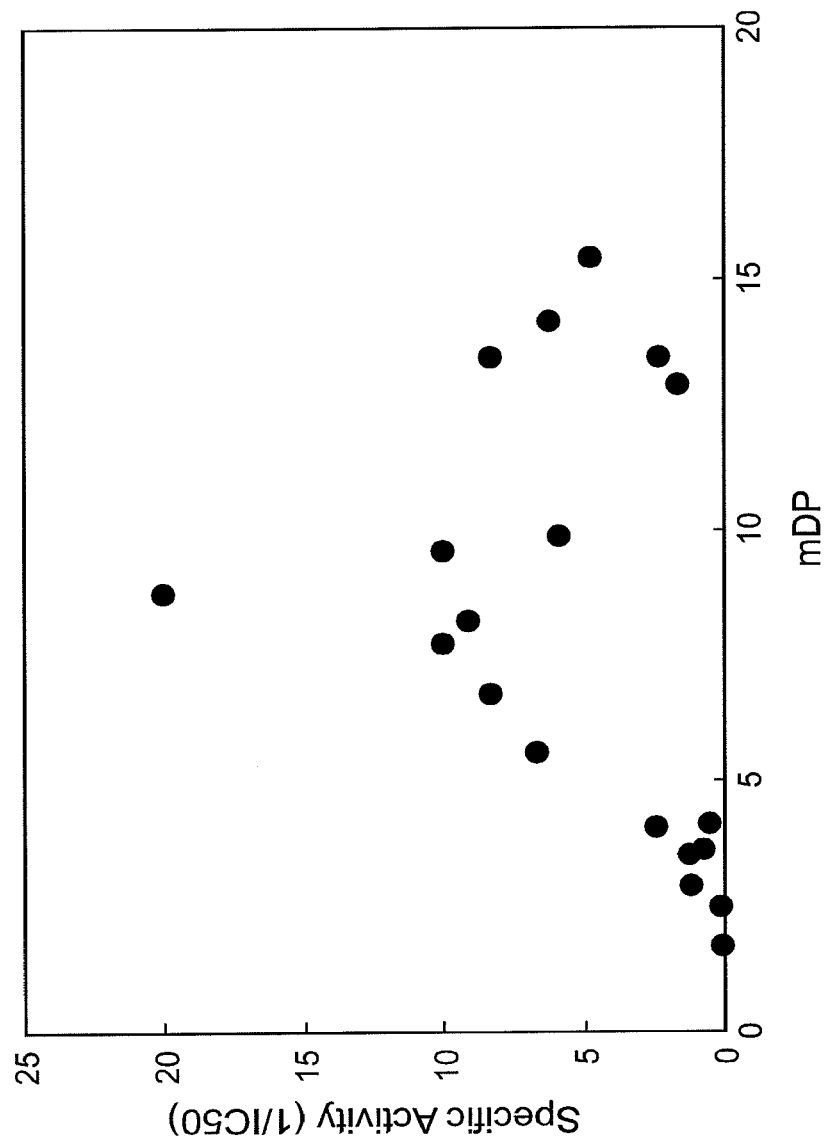
FIG. 11 shows the relationship with mean degree of polymerization (mDP) and specific activity (1/IC50) of Sephadex LH-20 fractionation from blueberry leaves.

In this invention, the mean polymerization degree of the PAC is preferably at least 5 in terms of anti-HCV production activity as shown in FIG. 11. However, if a PAC polymer composition contains at least 3 of monomer unit of the general formula (1) in the mean polymerization degree; its anti-HCV replicon production activity value is at most 1.0 μg/ml; the ratio of cytotoxicity activity value (CC50) divided by anti-HCV production activity value (IC50) is at least 10, such PAC polymer compositions are covered in this invention.

In this invention, the mean polymerization degree of the PAC means the average number of flavan-3-ol units bound each other with the bond pattern (i), (ii) and (iii). The number of flavan units can be determined by the method described in the example 1.

The PAC may be either synthetic product or natural product. The natural product can be derived from some plants containing polyphenol. It is known that some colored fruits and vegetables are high content of polyphenol. There can be illustrated by examples of blueberry leaves, grape seeds, taro, bilberry, elderberry, plum, blackberry, strawberry, redcurrant, blackcurrant, cranberry, cherry, raspberry, currant, a hibiscus flower, green pepper, beans, peas, soybean skin, a red cabbage, a purple corn, a purple sweet potato, herbs, fern, nuts, bark etc. Particularly, the blueberry leaves, the grape seeds and taro are very effective for the inhibitory activity of HCV production. The skin of Taro contains a large amount of proanthocyanidin. It may be practical to use the skin of Taro, in spite of the unsuitable part for eating.

Various parts of a plant or its processed good are also useful for the starting material of this invention. The usable starting material is, for example, leaves, petals, calyx, flowers, leafstalks, fresh tops, roots, stems, seeds, pods, rhizomes, barks, cambiums, lumbers, mycocecidium, fruits, tree saps, resin, a peel of grape, apple, onion, avocado and citrus; pomas of apple, wine, grain hull, straw and hay; the lumps from oily seeds derived from olive, oilseed rape and canola; and the extracts from other oily crops etc.

The most preferable starting material is blueberry shown in the example 1. The blueberry belonging to Cyanococcus of *Vaccinium* of Ericaceae is a deciduous or evergreen fruit tree, which is a low tree or a low bushes originally comes from America. The Usable blueberries in this invention are without reference to kinds and native localities thereof and are limited to the listed above. The blueberry is generally classified into around six kinds, among which the routine use of horticulture is said to be three kinds below.

(1) Highbush blueberry (*Vaccinium corymbosum* L.); O'Meer, sharp blue, Fordable, Reveille, Spartan, Darrow, Duke, Berkeley, Harrison etc.
(2) Rabbit eye blueberry (*V. Verbatim* Ayton); Woodard, Garden blue, Tubule, Home bell, Myers etc.
(3) Low bush blueberry (*V. angustifolium* Ayton, *V. metalloids* Michaud); Chengchow, Brunswick, Boliden etc.

Rabbiteye blueberry is most useful staring material among them listed above.

The PAC as effective ingredient in this invention can be produced by combination of following steps depending on intended use.

(1) Pretreatment step: First of all, blueberry leaves are washed with water and filtered to remove unusable miscellaneous things therefrom. The unwanted components such as cellulose, chlorophyll etc. in the crude material after washing are distilled away with organic solvent. As the organic solvent, chloroform, hexane, acetone etc. and the combination thereof can be properly used. The distillate may be supplied to next step directly or after pulverizing with or without drying. Extracted or squeezed juice from the crude material can also be supplied as well. Before supplying next step, the extracted or squeezed juice may be condensed, dried and pulverized into powder.

Any conventional dryer can be used in this invention, so long as changing nature of chemicals in the crude material. For instance, a vacuum-freeze dryer, a hot air dryer, a far-infrared radiation dryer, a reduced-pressure dryer, a microwave reduced-pressure dryer, a super-heated steam dryer etc. can be used. Among them, the vacuum-freeze dryer is more useful, because of having few effects on the nature of the chemicals. The Vacuum-freeze dryer should be used under the designated condition depending on the state of leaves to be processed. For example, in case of fresh leaves, it is desirable that freezing temperature is from −30 to −20° C.; drying temperature from −30 to 30° C.; and drying period 15 to 24 hours.

(2) Extract step: The processed material in the former steps is then extracted with a solvent or solvents through single or multiple steps. In the extract process, the solvents may be used either alone or the combination thereof. For example, water or polar solvent compatible with water can be preferably used. As the solvent compatible with water, there are lower alkyl alcohol with numbers of carbon 1 to 4, such as methanol, ethanol, propanol, butane etc. and polio such as ethylene glycol, butylenes glycol, propylene glycol, glycerin etc. Among them, lower alkyl alcohol such as methanol or ethanol may be practical in terms of safety.

Other organic solvent, such as acetone, diethyl ether, dioxin, acetonitrile, ethyl acetate, xylene, chloroform, toluene, hexane etc. can also be used. These solvents may be used in either single or the combination thereof, such as the combination of water and polar solvent compatible with water. For instance, the mixed solvent of acetone and ethyl ether can be used preferably in the ratio of 1:1 by v/v. It is general to use the mixture of water and polar solvent as the mixed aqueous solvent. As aqueous alkyl alcohol, aqueous methanol and ethanol may be preferably used. The alcohol content in the aqueous alcohol is in the range of 5 to 90 percents, preferably 30 to 90 percents, more preferably 50 to 90 percents. It is recommended to use mixed alcohol solvent containing water or acetone in this invention.

In the extraction process, the processed material in above steps is immersed in cool or warm solvent. It is usually extracted under warming and agitating and then filtrated to give extracted liquid. For example, the extraction may be preferably carried out using an aqueous alcohol solvent containing 80 volume percents of alcohol at room temperature and for immersion periods of 30 to 60 minutes depending on the extracting temperature. The extraction can be done by percolation method too.

(3) Purification step: The impure solid materials can be removed from the obtained extract by filtration or centrifugal separation to give pure filtrate, if needed. The filtrate may be supplied to the next step directly, or after partially condensed by distillation or dried. Further, these condensed or dried materials can be further purified by the method such as column method or fractionation method with solvent (See; WO2000-64883).

Taro (*Colossian esculent* Schott) usable in this invention as one of the material of the PAC belongs to Colossian, Tracheae, originated from the South Asia and is widely cultivated in the many varieties over the world. The root stocks and leaf stems have been mainly utilized for foodstuffs so far. Among tracheae, there is kanji (*Amorphophallus konjac*), which can be used as foodstuff after processing. In addition, there are several varieties in tracheae for appreciation too. It is known that the root stock of Tracheae plants contains mucking, galactic and potassium as effective ingredients. It is also reported that galactic has activity of brain cell and immunity. Potassium prevents high blood pressure due to removing sodium. But there have been no report on anti-HCV production activity of the root stock of Tracheae plants until now.

The root stocks of Tracheae plant are generally used after processing in this invention to realize effective anti-HCV production. As typical processing method of the root stocks, there are pulverization, dried pulverization, squeezation and solvent extraction.

In general, the root stocks are pulverized after drying or slicing before drying. The root stocks of Tracheae can be dried according to the drying method of blueberry leaves set forth above. The extraction process and purification process can also be carried out by the same way as blueberry leaves.

The PAC in this invention can be prepared into various formulations such as extracted solution, condensed solution, paste, and dried or semidried powder. The purified PAC is understandably higher anti-HVC production activity compared with crude extracts.

There is no appropriate evaluation system for anti-HCV production activity in vivo except chimera mouse, because HCV dose not infect all animals other than primates. In this invention, HCV replicon cell as known in vitro evaluation system of HCV replication (Lohmann V. et al., *Science* Vol. 285, p. 110-113, (1999)) is employed as alternative vivo evaluation method. HCV replicon cell comprises a structural protein translation region with core and envelop constituting virus particle, and non-structural protein translation region having function of virus genome replication etc. The HCV replicon cell may be made from the non-structural region. The replication of HCV-RNA in this system is measured as replication numbers of whole HCV-RNA infected with HCV.

The effective mean degree of polymerization (mDP) of the flavan unit in general formula (1) is at least 3 in integer value. As shown in table 1, no anti-HCV production activity is found in catechin (DP=1) and catechin dimmer (DP=2). These findings suggest that other epicatechin, afzelechin and epiafzelechin would be few activity of anti-HCV production too.

TABLE 1

The activity of inhibiting replicon production

HCV Replication Suppressive Activity of Catechin Monomer and Epicatechin Dimer

| | Replication suppressive activity IC50(μg/ml) | Cytotoxicity CC50(μm/ml) | Ratio CC50/IC50 |
|---|---|---|---|
| Catechin | 16.18 | 100.4 | 6.2 |
| Epicatechin | 27.32 | 113.8 | 4.2 |
| Procyanidin B2 | >25.0 | >25.0 | — |

This invention encompasses PAC polymer composition wherein the position $R_2$ of flavan unit in the general formula (1) is hydroxyl; the position $R_1$ and the position $R_3$ are hydrogen or hydroxyl; and the position $R_4$ is hydrogen or modified groups, so far as the proportion of both $R_1$ and $R_3$ being hydroxyl is at most 40 percents of whole polymer composition. The anti-HCV production activity of gallocatechin and epigallocatechin so called generally prodelphinidin wherein all the position $R_1$, $R_2$ and $R_3$ in B-ring of the flavan unit are hydroxyl is likely quantity dependant inverse proportion as illustrated in the table 2. For instance, in case the proportion of the flavan units such as croton sap exceeds 40 percents of whole polymer composition, such polymer composition becomes stronger in cytotoxicity and less than or equivalent to 10 in the ratio between IC50 and CC50 as shown in the table 3 of the example 1. Accordingly, the polymer composition is unusable in practice as the inhibitor of HCV production in this invention.

The PAC of this invention may be produced chemically or biologically. The PAC is also purified directly from the natural material such as plants, provided that its structure and function fall within the scope defined in this invention.

The PAC may be supplied to end users in various formulations such as extracted solution, condensed solution, and dried or semidried powder etc. depending on their request.

The inhibitory agents of HCV production in this invention may be available directly, or as either prodrug or formulated medicine. The PAC may be administered to persons infected with HCV, in the form of either polymer composition alone as shown in the general formula (1), or together with medically acceptable salts, hydrates and solvates. In general, it seems to be rather effective to dose a drug comprising the PAC and pharmacologically and pharmaceutically acceptable additives.

As the pharmacologically and pharmaceutically acceptable additives, there may be diluent, disintegrant, auxiliary disintegrant, binder, lubricant, coating, pigment, base agent, solvent, auxiliary solvent, isotonic agent, pH regulator, stabilizer, injection agent, adhesive and so on.

When using the PAC as a drug, it is desirable to administrate in every dosing unit. As such dosing manner, there are oral administration, enteral administration, intravenous administration, local administration such as dermal administration, and interstitial administration such as subcutaneous administration, intramuscular administration etc.

As solid dosage formulation for oral administration, there may be tablet, ball, capsule, subtle granule or pill. In addition, there may be acceptable emulsion, suspension, and syrups as liquid dosage formulation for oral administration. When formulating drugs, lubricant, colorant, flavoring agent, and/or pH regulator can be added to the base agent including the PAC. The tablet may be coated with conventional sugar coating, gelatin coating, enteric coating tablet, film coating, double coating and multiple coating, if required. As the additives, there may be used diluents such as lactose, sucrose, sodium chloride, glucose, urea, starch, calcium carbonate, kaolin, crystalline cellulose, hydrated silica etc.; binders such as water, ethanol, propanol, sirup, glucose solution, starch solution, gelatin solution, carboxymethyl cellulose, shellac, methyl cellulose, potassium phosphate, polyvinyl pyrolidone etc.; disintegrants such as dried starch, sodium argininate, agar powder, laminarin powder, sodium hydrogen carbonate, calcium carbonate, polyoxyethylene sorbitan fatty acid ester, sodium lauryl sulfate, stearic acid monoglyceride, starch, lactose etc.; disintegrant suppressing agent such as sucrose, stearin, cacao butter, hydrogenated oil etc.; adsorption promoter such as quaternary ammonium salts, sodium lauryl sulfate etc.; humectants such as glycerin, starch etc.; absorbents such as starch, lactose, kaolin, bentonite, colloidal hydrated silica etc.; and lubricants such as purified talc, stearate, boric acid powder etc.

As the enteral administration, there may be the use of injectable products. When preparing the injectable products, it can be made in formulation of nontoxic solution, suspension or emulsion preferably sterilized and adjusted to the isotonicity nearly equal to blood. These suspension and emulsion can be prepared by using water; ethanol, propylene glycol, ethoxyisostearyl alcohol, polyoxyisosteayl alcohol etc; and/or polyoxyethylene sorbitan fatty acid ester. Further, there can be added sufficient amounts of salt, glucose and/or glycerin etc so as to obtain isotonic solution. In addition, usual solubilizing agents, buffering agents, pH regulating agents, soothing agents and the like can also be used. The injectable product can be administered under skin, into muscle or vein.

For local administration, there may be topical solution, cream, powder, paste, gellant and ointment. These are prepared by combining a given quantity of the effective ingredients including the PAC, and its pharmacologically and pharmaceutically acceptable prodrug or salts, together with additive usable for topical medicine such as fragrance, colorant, filler, surfactant, humectant, emollient, gellant, carrier, preserving agent and/or stabilizer.

For the formulation of interstitial administration, a suppository is typical. When preparing the suppository, there can be used higher alcohol; higher ester such as myristicin palmitate ester, polyethylene glycol, cacao butter, gelatin, semi synthetic glyceride and their mixture as substrates with low melting point. The suppository can be formulated by adding the PAC, its prodrug and their medically acceptable salt to these substrates.

When ministering the PAC or the inhibitory agent of HCV production containing its prodrug with their medically acceptable salt to patients needed thereof, the effective dosing quantity should be determined in view of condition of each patient of which condition are, for instance, a time of life, weight, the route of administration, the nature or level of disease etc. This invention suggests that the effective dosing quantities may be within the range of 1 to 2000 mg per a day for an adult human. But, according to clinical condition of a patient, the effective dosing quantities may be less than or larger than the suggested range. When dosing larger quantities than the suggested range, it is desirable to dose fractionally at several times per a day. The agent of this invention can also be adopted for preventing or inhibiting onset or progress of hepatic inflammation and cirrhosis, or treating hepatitis diseases arisen from HCV, in addition to the inhibition of HCV production that is the primary activity of this invention.

In case of pharmaceutical agent, the effective quantity of administration to a patient can not be determined strictly owing to variable dependant on the expected effect of treatment, administration method or its root, dosing periods, gender of a patient, and other condition of disease. Typically, the dosing quantities of the anti-HCV inhibitor including crude or purified production of this invention may be selected from the range about 100 to 1000 mg per a dose for the weight of 60 kg in a human patient as reduced weight of the purified PAC of this invention. The content of the PAC in the agent may be selected from the range of 0.1 to 99.5 weight percents, preferably 0.5 to 90 weight percents, though the content is needed not to specifically limit, because of variable dependant on the dosing quantities. Whenever necessary, the agent of this invention can be dosed. But, it is effective to dose in acute or chronic stage of hepatitis inflammation or stage of cirrhosis during which the state of hepatic disease is in progress.

Further, the PAC of this invention may be usable for dietary supplements such as food or drink. The supplements can be prepared in solid, liquid solution, emulsion and so on, and shaped into various forms such as tablet, ball, capsule, granule, powder, pastille, cake, drink etc. According to need, pharmacologically, pharmaceutically and dietary acceptable additives can be added. The additives include other various medical substances or functional ingredients such as vitamin, other minor components and the like.

EXAMPLES

Following examples illustrate more detail embodiments of this invention without, however, limiting the invention in any way. In the working example, percent (%) means weight percent (w/w %), unless otherwise stated.

[Experimental Procedure]

In the working example, the HCV replication suppressive activity test (replicon assay) and cytotoxicity test were carried out as follows.

The HCV-replicon cell line was established by transducing sub-genomic RNA into human hepatoma Huh-7 cell cytoplasm. The sub-genomic RNA was prepared by replacing the translated region of HCV genome RNA structural proteins with firefly luciferase gene, internal ribosome entry site (IRES) of the encephalomyocarditis virus and neomycin phosphotransferase gene. The cell line obtained was used for assessment of production of HCV replicon RNA. The production quantity of HCV replicon RNA was measured by the luciferase assay method. (Lohmann et al., Science 285, (1999) 110; Sakamoto et al. Nat. Chem. Biol. 1, (2005) 333)

Anti-Replicon Activity Test (Replicon Assay)

In order to determine replication quantity of HCV-RNA, luciferase genes from firefly were transduced into HCV-RNA as a reporter gene. The gene transduction was carried out according to the method of Krieger et al. (See; Krieger et al. J. virol. 75, (2001) 4614) in such manner that luciferase genes were fused together neomycin-resistant genes beneath the IRES of HCV gene.

With this HCV subgenome, the replication efficiency of HCV could be estimated by measuring luciferase activity in the HCV replicon cells. The HCV replicon cells used were routinely grown in DMEM (Gibco cat. No. 10569-010) supplemented with Glutamax (Invitrogen), 10% fetal bovine serum (FBS), 1% penicillin/streptomycin (Invitrogen) and 500 µg/ml G418 (Invitrogen). The cells were maintained at 37° C. in humidified atmosphere containing 5% CO2. For the HCV replication assay, the replicon cells in DMEM supplemented with Glutamax and 5% FBS were seeded in a 96-well plate so as to fill every well with 5000 cells, and incubated for 24 hours.

The test was carried out in such a way that the HCV replicon cells were cultured for 72 hours after adding test samples in different concentrations. The Quantity of the luciferase activity was determined by the Steady-Glo Luciferase Assay System (Promega) according to the manufacture's instructions and the luminescence was measured by DTX 800 Multimode Detector (Beckman). In this test, the replication inhibitory activity is expressed as a concentration of samples required for inhibiting 50 percents of the replication of HCV replicon cell (IC50). Specific activity is a reciprocal number of IC50 (1/IC50). Total activity is calculated by multiplying the yield weight of the HCV replicon cell by specific activity.

Cytotoxicity Test

The cytotoxicity of the samples was measured by Cell Counting Kit-8 (CCK-8; Dojindo Molecular Technologies) according to the manufacture's instructions. Briefly, 10 µl/a well of CCK-8 reagent were added to the HCV replicon cells cultured in a 96-well plate and then incubated at 37° C. for 60 min. The absorbance of each well was measured at 450 nm with a reference wavelength at 650 nm using an Emax Precision microplate reader (Molecular Devices Inc.). Cell viability was calculated as relative index of control cells and effects of samples and was expressed as the concentration of samples required for 50% cytotoxicity of the cells (CC50).

FIG. 1 illustrates the results of a PAC sample from blueberry leaves in replicon assay. The IC50 value showing the replication suppressive activity was 0.56 µg/ml and the CC50 value showing the cytotoxicity was 16.26 µg/ml. The IC50 was less than or equal to 1.0 µg/ml and the ratio, which was calculated by dividing CC50 by IC50, was larger than or equal to 10. In conclusion, the PAC sample has the inhibitory activity of HCV replication.

Example 1

Identification of Effective Compounds for suppressing HCV replication contained in the blueberry leaves 1. Extraction and Liquid-Liquid Distribution One gram of the lyophilized powder, which made from the leaves of rabbit-eye blueberry (*Vaccinum virgatum* Ayton), was extracted with 100 ml of methanol at room temperature under shaking for 15 min, and the supernatant of the resultant extract was passed through filter paper (Toyo filter paper No. 2). The methanol extract was further extracted with 100 ml of chloroform, followed by the resultant precipitate and supernatant were collected. The precipitate was dissolved in methanol, concentrated in vacuo and lyophilized (CMW-ppt: 63.7 mg). The supernatant was mixed with 150 ml of distilled water and methanol to perform a liquid-liquid extraction, and the water layer was collected and mixed with 150 ml of chloroform so as to repeat the chloroform extraction. The water layer was concentrated and lyophilized (CMW-W: 284.2 mg). The chloroform layer was also concentrated and lyophilized (CMW-C, 56.3 mg).

The suppressing activity of HCV replication was not detected from the CMW-C fraction in replicon cell assay, but detected from the CMW-ppt and the CMW-W. In following purification, the CMW-W with a large recovered amount in weight and a large amount of total activity was used.

2. The Fractionation by HPLC (Confirmation of Elution Time by HPLC)

To separate the components in the CMW-W fraction possessing HCV replication inhibitory activity, fractionation and purification were performed using HPLC (Prominence System; Shimadzu) with UV detector and photodiode array detection (PDA). The other analytical condition shows as follows.

Instrument: Shimadzu Prominence LC-20A
Column: Atlantis dC18, 4.6 mm I.D.×150 mm, 3 μm (Waters), 40° C.
Eluent: (A) 0.05% (v/v) Trifluoroacetic acid
(B) Acetonitrile
Gradient: Eluent B. 15%(0 min)–25%(12.5 min)–100% (17.5 min)–100%(25 min)
Flow Rate: 0.7 ml/min
Detector: 254 nm 50 μl of the CMW-W fraction dissolved in 30 ml of methanol was injected into HPLC and the eluted total 26 fractions were collected during a period from 2.3 to 19.5 min. The replicon assay of collected each fraction was carried out in concentration of 1%, 5% and 10%.

Figure 2:
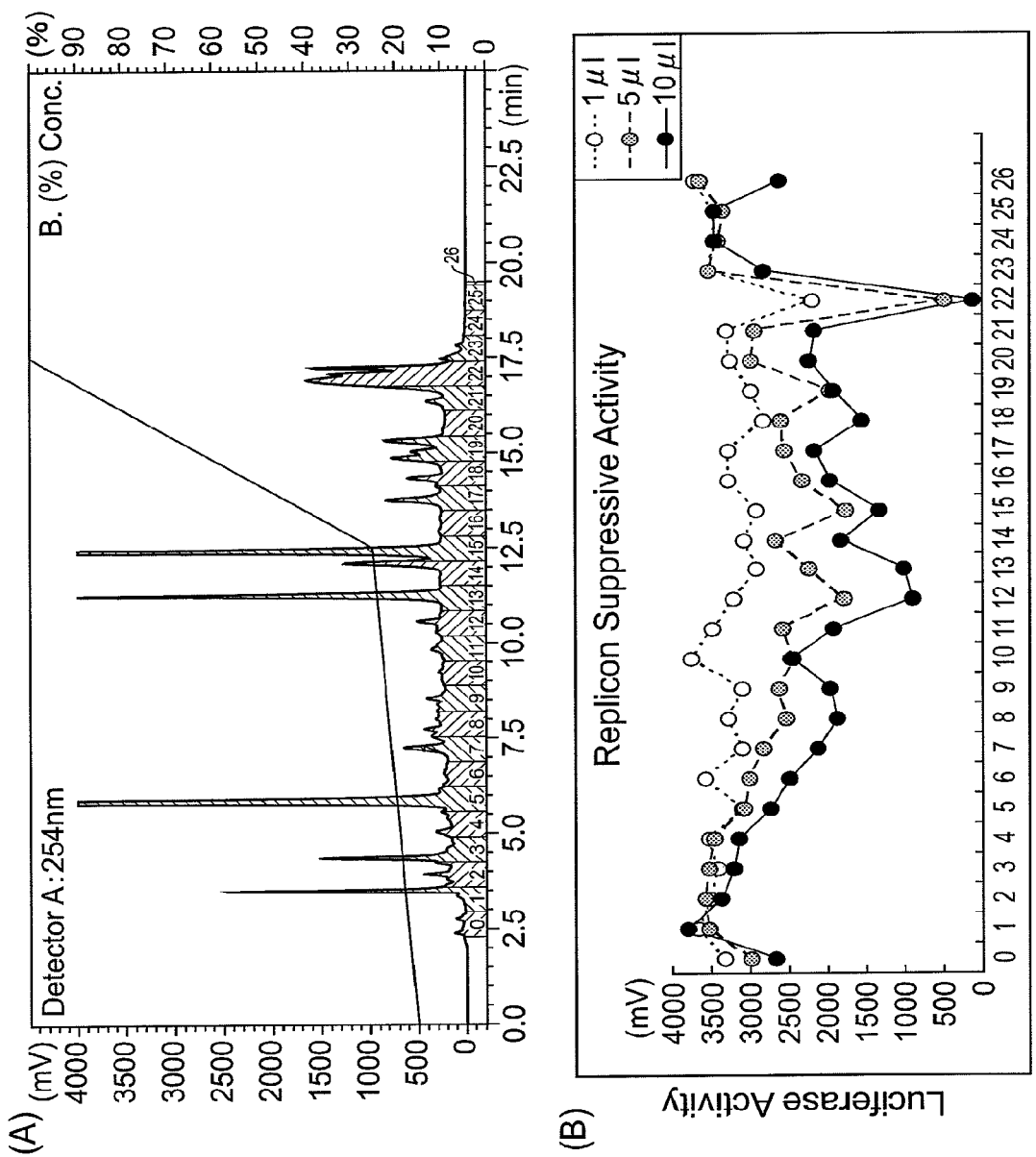
FIG. 2A shows HPLC chromatogram of methanol extract from blueberry leaves.
FIG. 2B shows the replication suppressive activity of fractionation by HPLC according to FIG. 2A.

FIGS. 2 (A) and (B) shows HPLC chromatogram and activity of suppressed replication for collected fraction, respectively. The data indicated that a fraction having strong replication inhibitory activity and eluted by around 90% of acetonitrile at 17 min contains some week inhibitory activity fractions same as broadly eluted fraction earlier. Those results suggested the possible existence of multiple replication inhibitors in CMW-W fraction. However, the chlorogenic acid and the rutin included lots in blueberry leaves and eluted at around 6 and 11 min respectively were seem not to have the inhibition activity aforementioned.

Figure 3:
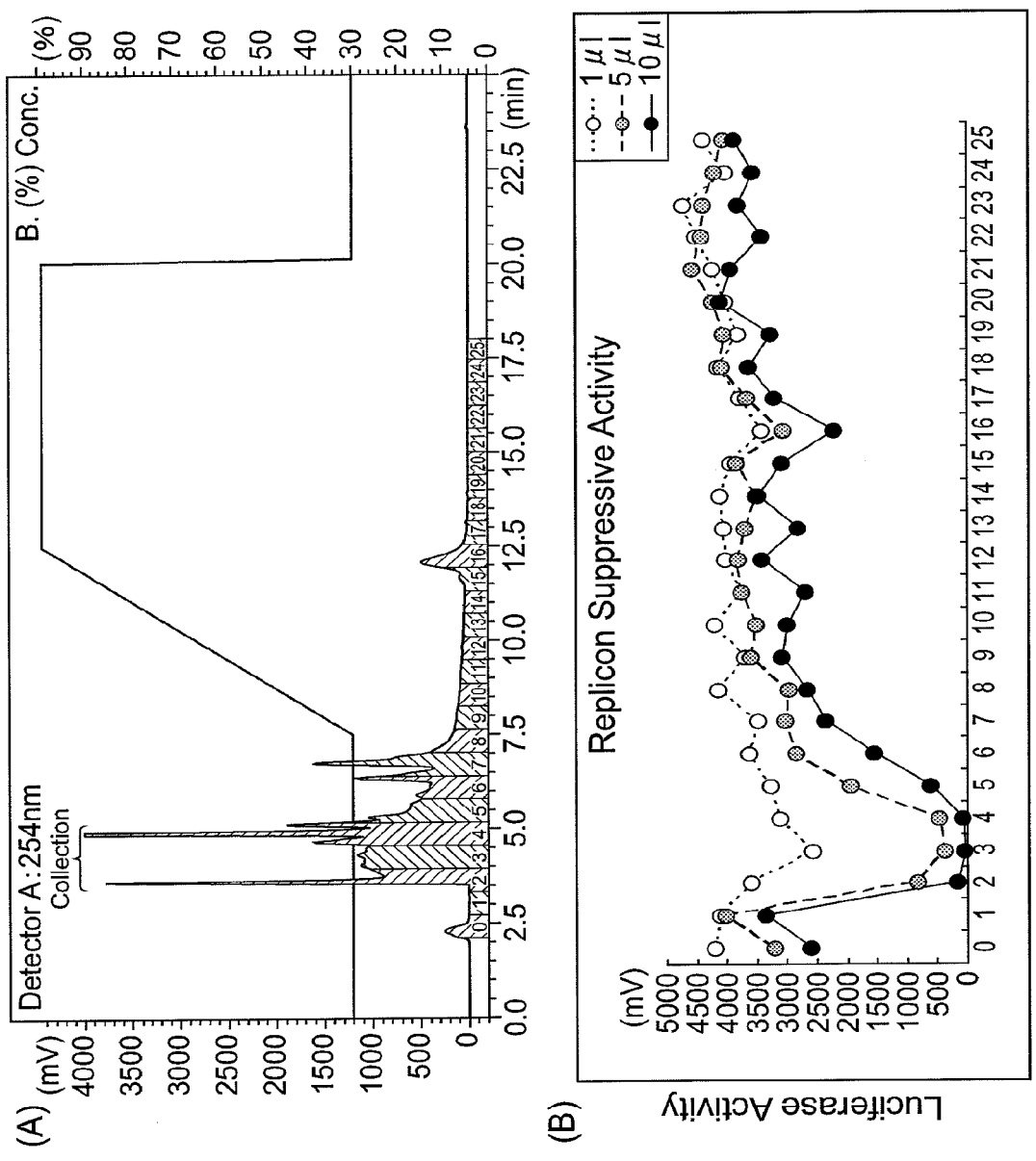
FIG. 3A shows HPLC chromatogram of 1st fractionation (LC1) of methanol extract from blueberry leaves.
FIG. 3B shows the replication suppressive activity of LC1 by HPLC according to FIG. 3A.

(1st Fractionation) The 1st Fractionation Performed Under the Following Condition.
Column: Atlantis T3, 4.6 mm I.D.×150 mm, 3 μm (Waters), 40° C.
Eluent: (A) 0.05% (v/v) Trifluoroacetic acid
(B) Acetonitrile
Gradient: Eluent B. 30%(0 min)–30%(7.5 min)–100% (12.5 min)–100%(20 min)
Flow Rate: 0.7 ml/min
Detector: 254 nm 100 μl of the CMW-W fraction was injected into HPLC system and the eluted 26 fractions during from 2.1 to 18 min were collected. FIG. 3 shows the results of HPLC chromatogram and replicon assay in the collected fractions.

In order to purify the most active component, the CM was separated into isocratic condition at 30% acetonitrile and the eluate from 3.3 to 5.2 min, and then the latter was collected. After repeating collection, 140.2 mg as active fraction (LC1) was obtained from 440 mg of methanol extracts. The IC50 value of this fraction in the HCV replication assay was 0.89 μg/ml and the yield of specific activity was 6-fold higher than that of the initial methanol extracts (TABLE 2).

Figure 4:
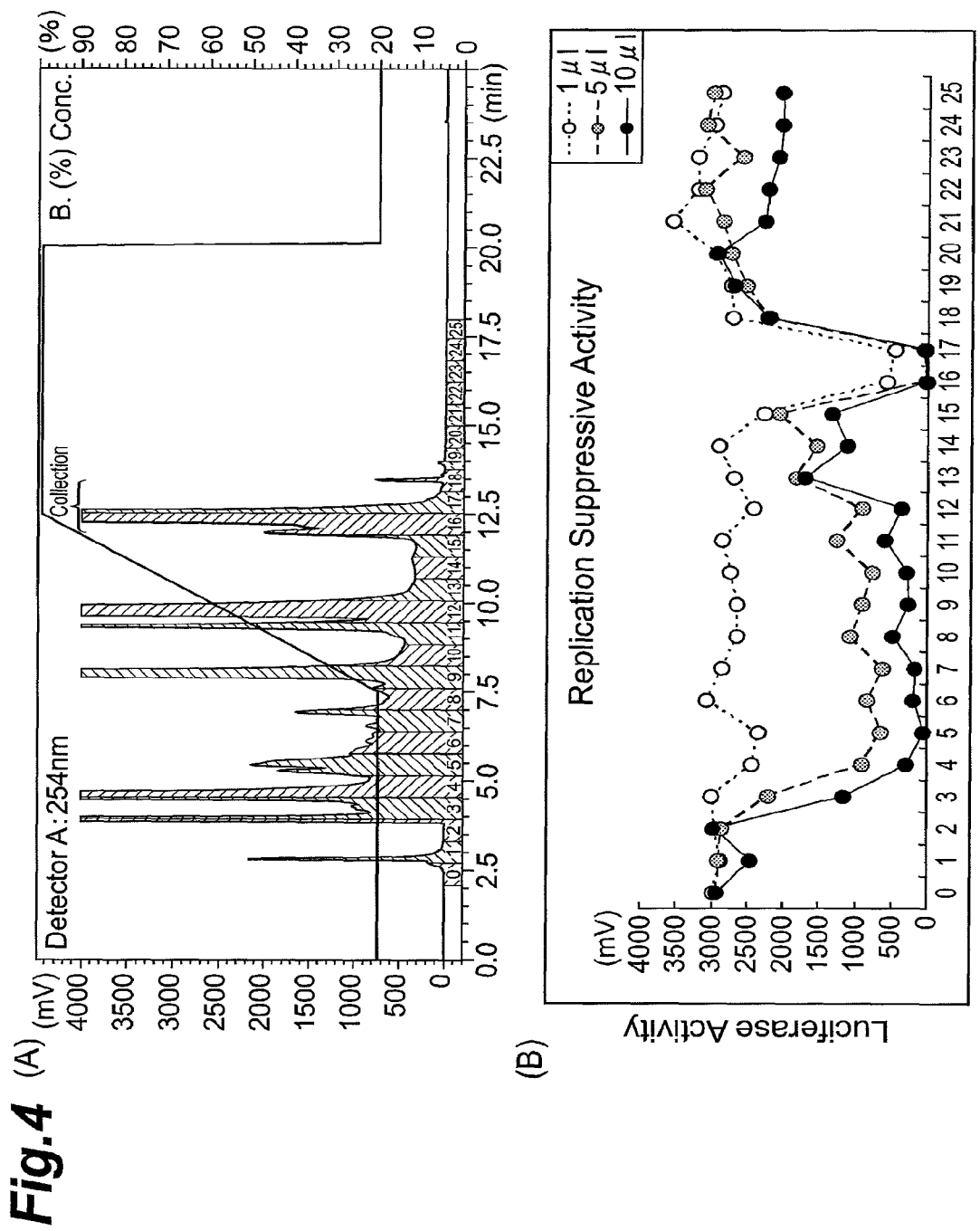
FIG. 4A shows HPLC chromatogram of 2nd fractionation (LC2) of LC1.
FIG. 4B shows the replication suppressive activity of LC2 by HPLC according to FIG. 4A.

(2nd Fractionation) The 2nd Fractionation Performed Under the Following Condition.
Column: Atlantis T3, 4.6 mm I.D.×150 mm, 3 μm (Waters), 40° C.
Eluent: (A) 0.05% (v/v) Trifluoroacetic acid
(B) Acetonitrile
Gradient: Eluent B. 20%(0 min)–20%(7.5 min)–100% (12.5 min)–100%(20 min)
Flow Rate: 0.7 ml/min
Detector: 254 nm The active fraction (LC1) of 140.2 mg obtained from 1st fractionation was dissolved in 11 ml of methanol. The solution obtained was injected into HPLC system. The eluted fraction was collected from 2.1 to 18 min (Total 26 fractions). FIG. 4 shows HPLC chromatogram and replicon assay of collected fractions.

In the second round HPLC, a highly active fraction was eluted from 11.9 to 13.2 min and collected (LC2), yielding 24.6 mg with an 1050 value 0.54 μg/ml (TABLE 2).

Figure 5:
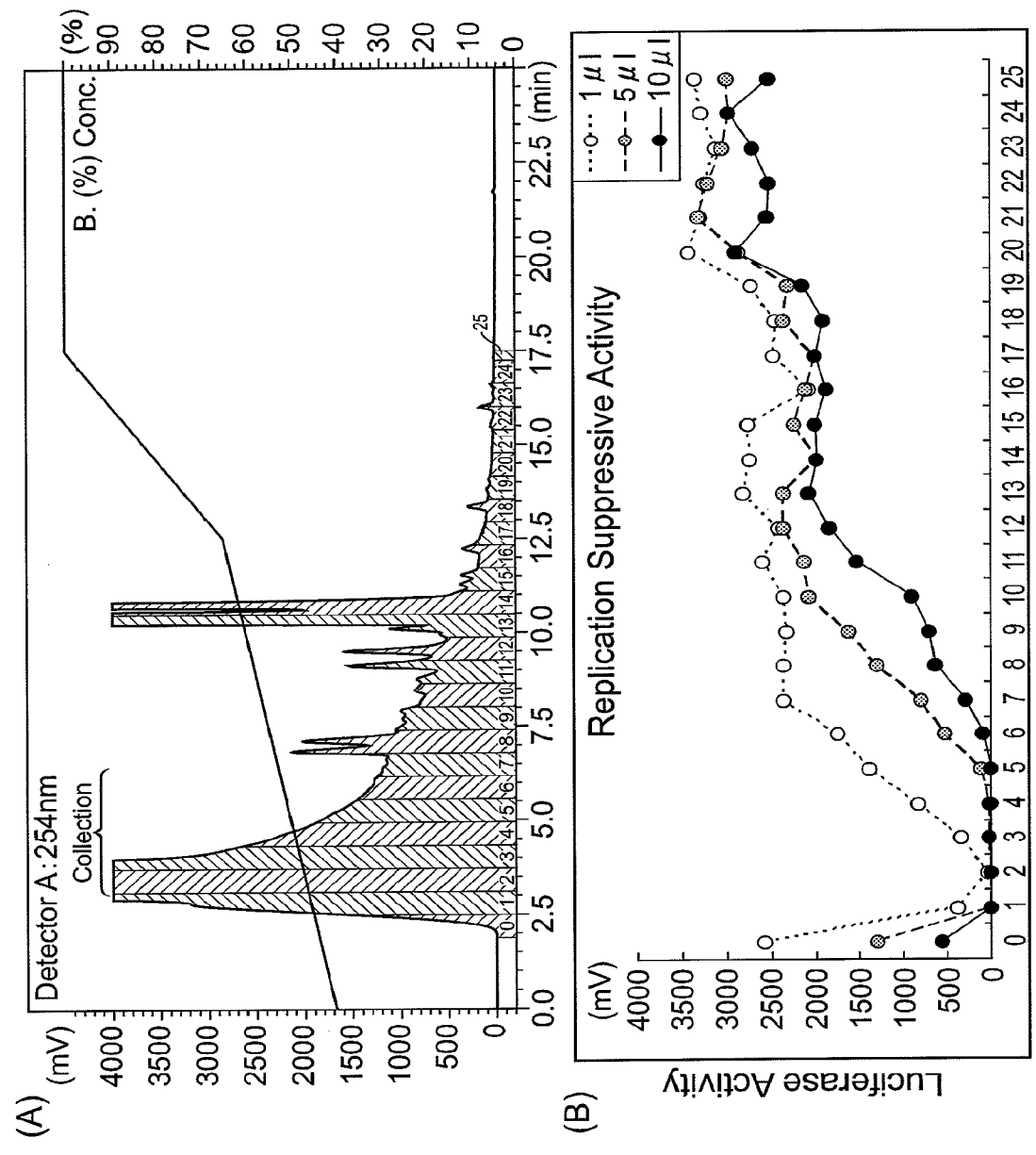
FIG. 5A shows HPLC chromatogram of 3rd fractionation (LC3) of LC2.
FIG. 5B shows the replication suppressive activity of LC3 by HPLC according to FIG. 5A.

(3rd Fractionation) In the 3rd Fractionation, the Eluent B was Replaced by Methanol and Eluted with 40-65% B Linear Gradient Under the Following Condition.
Column: Atlantis T3, 4.6 mm I.D.×150 mm, 3 μm (Waters), 40° C.
Eluent: (A) 0.05% (v/v) Trifluoroacetic acid
(B) Methanol
Gradient: Eluent B. 40%(0 min)–65%(12.5 min)–100% (17.5 min)–100%(25 min)
Flow Rate: 0.7 ml/min
Detector: 254 nm 24.6 mg of the active fraction (LC2) were dissolved in 2.5 ml of methanol. The LC2 methanol solution was injected into HPLC system. The eluted fraction was collected from 2.3 to 17.5 min (total 26 fractions). FIG. 5 shows HPLC chromatogram and replicon assay of collected fractions.

The active fraction was eluted during from 3.2 to 6.2 min and collected (LC3). The finally yielded solid material of 2.9 mg had a dark flesh color.

TABLE 2 shows an overall purification steps from blueberry leaves. From 1000 mg of lyophilized powder of the leaves, 440 mg of methanol extracts were obtained. The IC50 value of methanol extracts was 5.47 μg/ml. From the 284.2 mg of the CMW-W fraction was found out the replication inhibitory activity wherein the IC50 value was 1.74 μg/ml; the specific activity of the CMW-W was 3-fold greater than that of the initial extracts; and the yield of the activity exceeded 200%. These values result from that the interfering substances had been removed from the test sample.

The final fraction which was purified by repeated fractionation in reversed-phase HPLC showed a 63-fold increase in specific activity compared with the initial methanol extracts. The CC50 value of the cytotoxicity of LC3 was 18.5 μg/ml and the ratio was 212.6 that was a 16.5-fold higher ratio compared with initial extracts.

TABLE 2

Purification Steps from Blueberry Leaves

| | Total Weight (mg) | IC50 (μg/ml) | Specific Activity (1/IC50) | Purification Factor | Total Activity (mg/IC50) | Yield (%) |
|---|---|---|---|---|---|---|
| MeOH Extract | 440.0 | 5.47 | 0.18 | 1.00 | 80.44 | 100 |
| Water Layer | 284.2 | 1.74 | 0.57 | 3.14 | 163.33 | 203.05 |
| LC1 | 140.2 | 0.89 | 1.12 | 6.15 | 157.53 | 195.84 |
| LC2 | 24.6 | 0.54 | 1.85 | 10.13 | 45.56 | 56.63 |
| LC3 | 2.9 | 0.087 | 11.49 | 62.87 | 33.33 | 41.44 |

3. The Elemental Composition Analysis of Electron Probe Micro-Analysis (EPMA)

Figure 6:
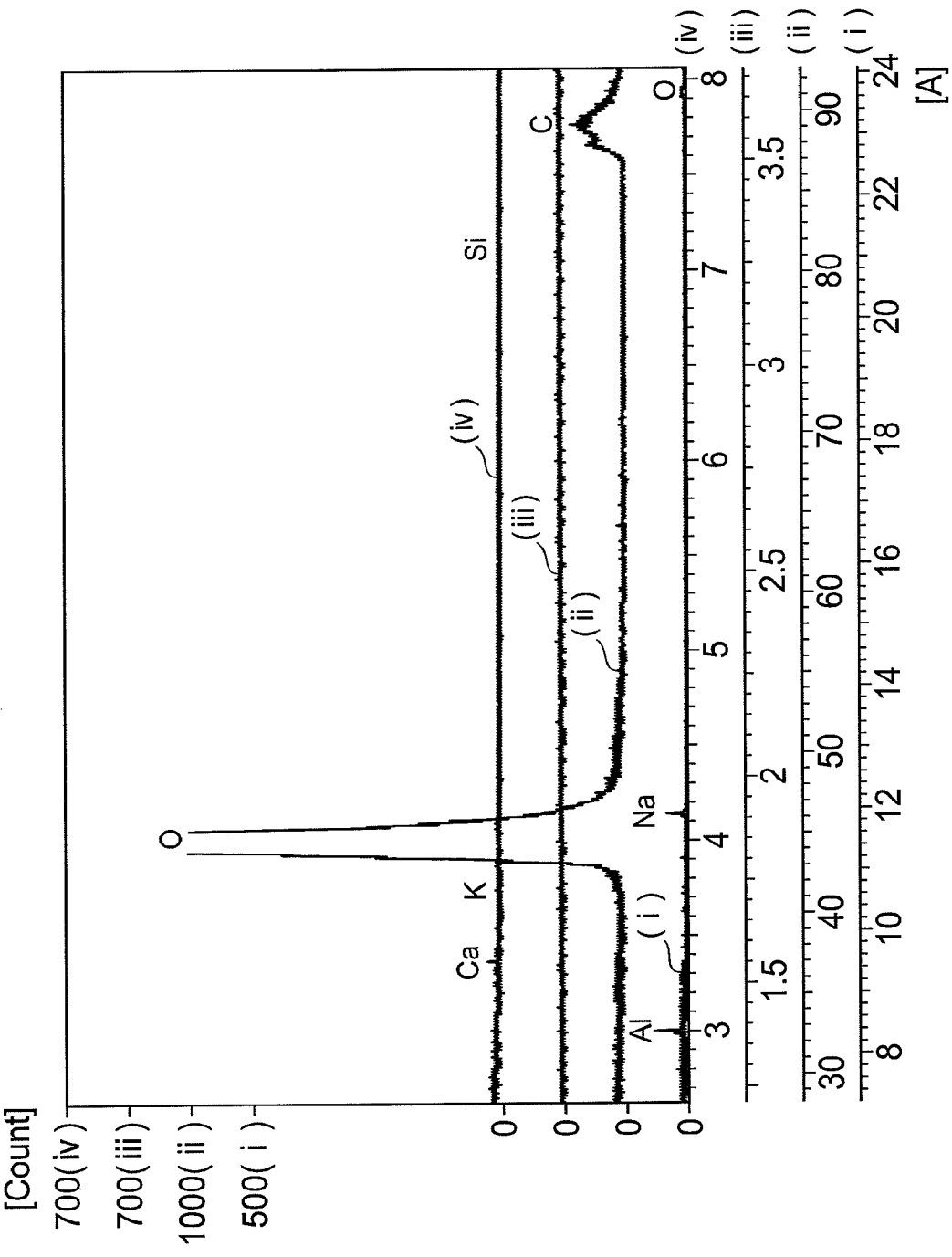
FIG. 6 shows elemental composition analysis of LC3 (purified fraction from blueberry leaves) by electron probe microanalysis (EPMA)

For EPMA (EPMA-1600, Shimadzu), the excitation voltage and the beam current were kept at 15 kV and at 100 nA, respectively. The diameter of the electron beam was 50 μm and the sample was processed for carbon shadowing in advance. In order to determine the constituent elements, the purified fraction (LC3) was analyzed by EPMA. This analysis indicates that the fraction is composed of carbon, oxygen and hydrogen, but not nitrogen (FIG. 6).

4. The Constitutive Analysis of Liquid Chromatography/Mass Spectrometry-Ion Trap-Time of Flight (LC/MS-IT-TOF)

Identification of the anti-HCV replication fraction (LC3) purified from blueberry leaves was done by HPLC-MSn fragmentation analysis. An HPLC (Prominence System; Shimadzu) on a reverse-phase column was equipped with a PDA detector scanning from 200 to 800 nm and mass spectrometry-ion trap-time of flight (MS-IT-TOF; Shimadzu) detector. The instrument and analysis condition show as follows.

Instrument: Shimadzu LC/MS-IT-TOF
Column: Atlantis T3, 2.1 mm I.D.×100 mm, 3 μm (Waters), 40° C.
Eluent: (A) 0.05% (v/v) Trifluoroacetic acid
(B) acetonitrile
Gradient: Eluent B. 10%(0 min)–25%(7.5 min)–100% (12.5 min)–100%(20 min)
Flow Rate: 0.25 ml/min
Detector A: PDA 280 nm
Detector B: Atmospheric pressure chemical ionization (APCI)-MS (Negative-ion Mode; interface voltage, −3.0 kV, interface temperature, 450° C.; curved desolvation line (CDL) temperature, 200° C.; nebulizer N2 gas, 2.0 L/min; drying N2 pressure, 70 kPa; heat block temperature, 200° C.)

In the preliminary trials of LC/MS analysis, the electrospray ionization (ESI) was used as ionized probe, but the target compounds were not able to observe in mass spectrum. When exchanging the ionization probe for APCI and setting the interface temperature at 450° C., the mass spectrum of target compounds could be found out.

Figure 7:
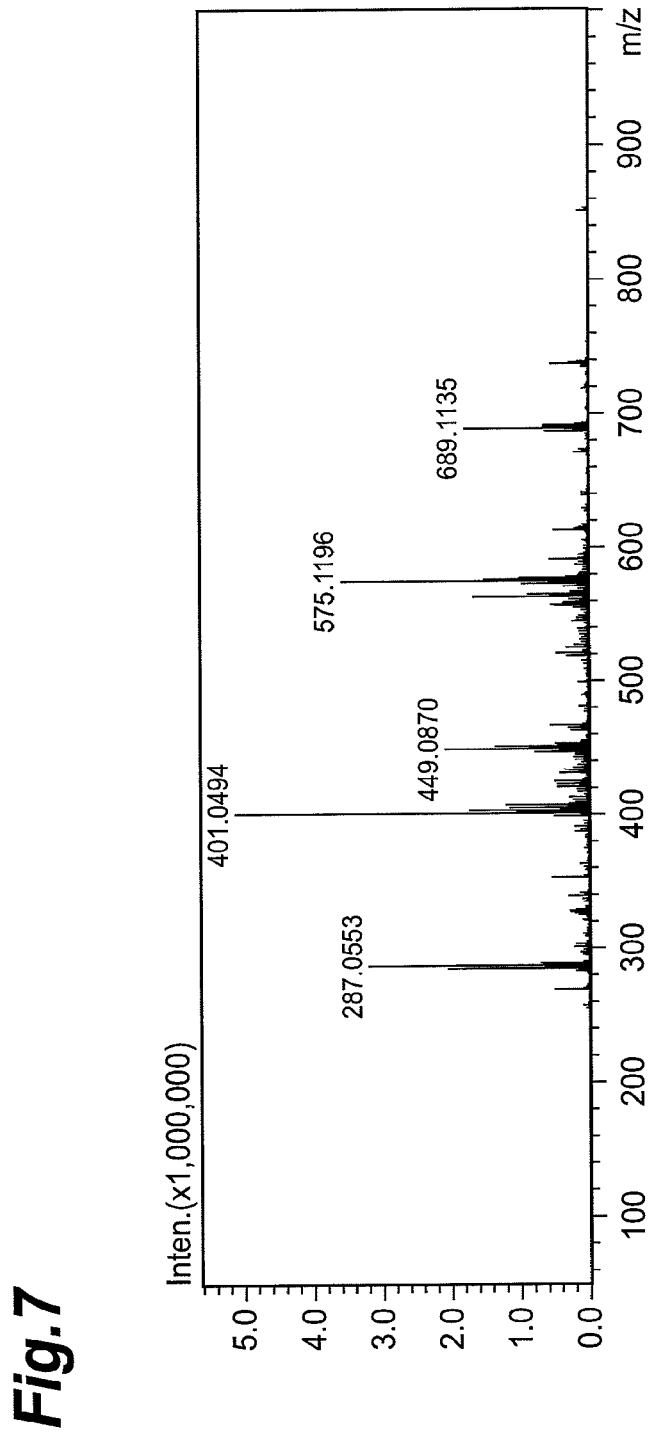
FIG. 7 shows mass spectrum of LC3 (purified fraction from blueberry leaves) by LC/APCI-MS-IT-TOF

The mass spectrum data shows five peaks (FIG. 7). The [M-H]− at m/z 401.0494 and 689.1135 were considered to be trifluoroacetic acid adducts of m/z 287.0553 and 575.1196 respectively. From these spectra, the parent mass of this compound appeared to be [M-H]− at m/z 575.1196, which was estimated to be $C_{30}H_{24}O_{12}$ (error=0.17 ppm) that is an A-type dimer of procyanidin. Given the fact that strict conditions (APCI probe temperature at 450° C.) were required to ionize the compound, it appeared that the isolate was composed of one or more polymers of procyanidin.

5. Identification of Proanthocyanidin (PAC) by Butanol-HCl Method (Porter Method)

PAC were characterized by a modified method of Porter et al. (Porter et al., Phytochem. 25, (1986) 223; Shoji et al., J. Agric. Food Chem. 54, (2006) 884)

Heating PAC under acidic condition, carbenium ion and catechin are produced by disconnecting the interflavan-bond thereof. The former are more oxidized to give a red anthocyanidin. The porter method based on the principle of these color reaction is able to perceptively detect PAC from samples in increasing absorbance at 540 nm.

(1) Quantitative Determination and Qualitative Analysis of PAC by Porter Method

200 μl of the purified compound from blueberry leaves was mixed with 750 μl of n-butanol/HCl (95:5) and 50 μl of 1% of $NH_4Fe(SO_4)_2.12H_2O$ dissolved in 2M HCl. The mixture was vortexed and heated in an oven at 105° C. for 40 min and cooled in flowing water. Optical densities of the treated solution were recorded at 540 nm by spectrophotometer (UV-1700, Shimadzu). Procyanidin B2 (Sigma-Aldrich) was used as a standard.

(2) LC/MS Analysis of Porter Method Products

The hydrolysates generated by the modified Porter method were also analyzed using LC/MS-IT-TOF as follows.

Instrument: Shimadzu LC/MS-IT-TOF
Column: Atlantis. T3, 2.1 mm I.D.×100 mm, 3 μm (Waters), 40° C.
Eluent: (A) 0.5% (v/v) Formic acid containing 5 mM Ammonium Formate
(B) acetonitrile
Gradient: Eluent B. 10%(0 min)–40%(15 min)–100%(15 min)–100%(22.5 min)
Flow Rate: 0.25 ml/min
Detector A: PDA 540 nm
Detector B: ESI-MS (Positive-ion Mode; interface voltage, 4.5 kV, interface temperature, 200° C.; curved desolvation line (CDL) temperature, 200° C.; nebulizer N2 gas, 1.5 L/min; drying N2 pressure, 200 kPa; heat block temperature, 200° C.)

Figure 8:
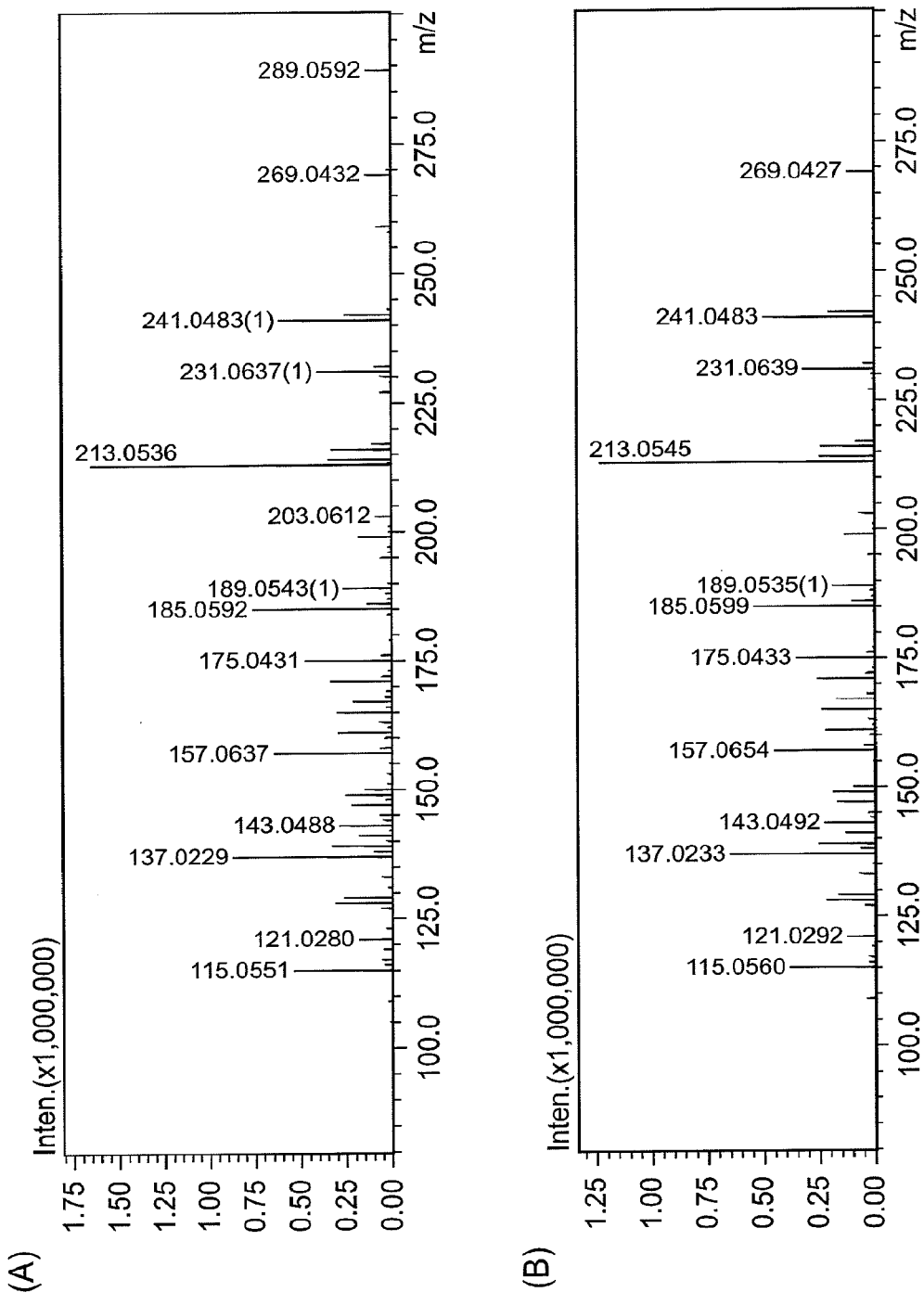
FIG. 8A shows MS/MS spectrum of cyanidin preparation by LC/ESI-MS.
FIG. 8B shows MS/MS spectrum of LC3 (purified fraction from blueberry leaves) by LC/ESI-MS.

The purified LC3 fraction was analyzed by Porter method. The reacted solution turned a red color, which corresponds to the color of anthocyanidin generated by heating of procyanidin/proanthocyanidin mixture under acidic conditions. Using procyanidin B2 as the standard, the procyanidin content in the LC3 fraction was 86.33%. The hydrolysis solution was analyzed by LC/MS-IT-TOF. The main peak (RT=7.3 min) of the PDA chromatogram at 540 nm was observed at the same position as that of the cyanidin standard (FIG. 8A). Indeed, MS/MS spectra of this peak were identical to those of the cyanidin standard (FIG. 8B). These results revealed that the HCV replication inhibitory compound in the LC3 fraction from blueberry leaves was procyanidin and its derivatives. As the hydrolysate of this compound also contained a trace amount of delphinidin, these compounds was considered to be proanthocyanidin rather than procyanidin.

6. Analysis of Mean Degree of Polymerization (mDP) and Composition Units for PAC by Thiolysis Thiolysis was performed by previously described method with some modifications (Guyot et al., J. Agric. Food Chem. 49, (2001) 14; Gu et al., J. Agric. Food Chem. 50, (2002) 4852). Briefly, 50 μl of PAC samples (2 mg/ml in methanol) was mixed with 50 μl of methanol acidified with HCl (3.3%) and 100 μl of benzylmercaptan (5% in methanol). The reaction was carried out at 50° C. for 30 min and then kept at ambient temperature for 3 hours. Pure catechin or epicatechin solution (1.25 mg/ml in methanol, Funakoshi) was also thiolysed to obtain the epimerization rate by calculating the ratio of catechin and epicatechin in the terminal units. The reaction mixture was diluted 5-fold with methanol and analyzed by reverse-phase HPLC as follows.

Column: Atlantis T3, 4.6 mm I.D.×150 mm, 3 μm (Waters), 40° C.
Eluent: (A) 0.05% (v/v) Trifluoroacetic acid
(B) Acetonitrile
Gradient: Eluent B. 15%(0 min)–25%(10 min)–100%(40 min)–100% (45 min)
Flow Rate: 0.7 ml/min
Detector: 280 nm To ascertain the elution pattern of thiolysis media and to estimate unknown peaks, LC/MS-IT-TOF was also employed in a negative ion mode. The instrument and analysis condition show as follows.

Instrument: Shimadzu LC/MS-IT-TOF

Column: Atlantis T3, 2.1 mm I.D.×100 mm, 3 μm (Waters), 40° C.

Eluent: (A) 0.05% (v/v) Trifluoroacetic acid
(B) acetonitrile

Gradient: Eluent B. 15%(0 min)–25%(10 min)–60%(40 min)–100%(40 min)

Flow Rate: 0.25 ml/min

Detector A: PDA 280 nm

Detector B: ESI-MS (Negative-ion Mode; interface voltage, −3.0 kV, interface temperature, 200° C.; curved desolvation line (CDL) temperature, 200° C.; nebulizer N2 gas, 1.5 L/min; drying N2 pressure, 200 kPa; heat block temperature, 200° C.)

Figure 9:
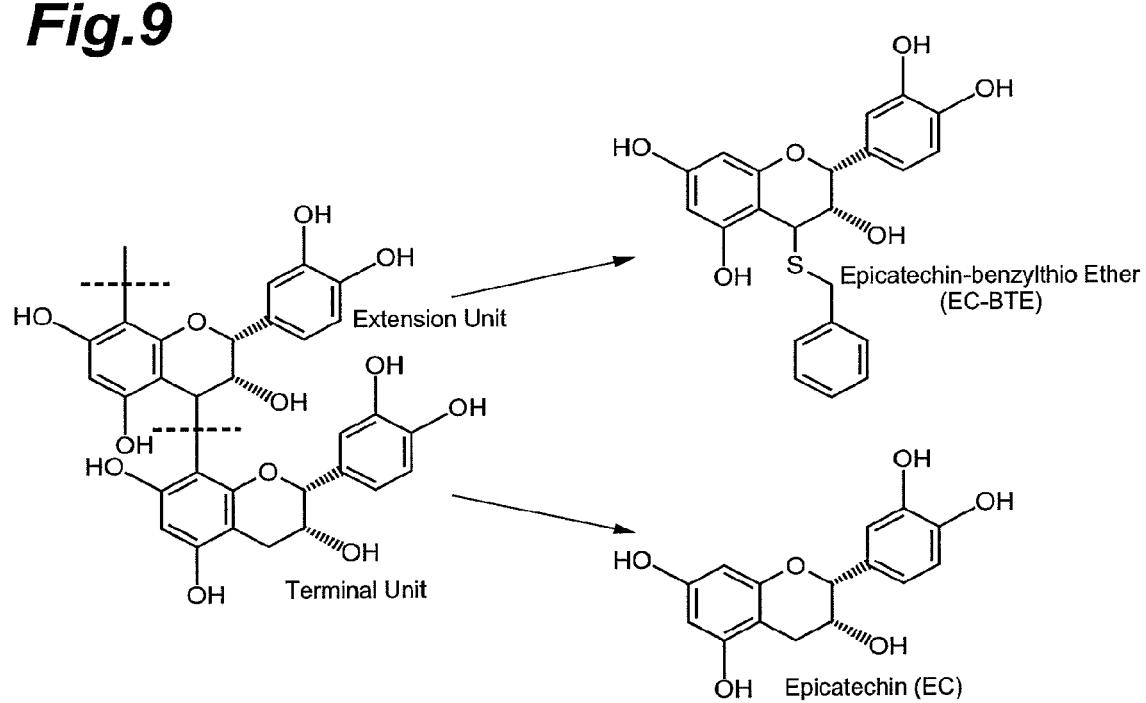
FIG. 9 shows thiolysis reaction pattern of PAC reacted with benzylmercaptan under acidic condition.

Flavan-3-ols and their benzylthio adducts obtained by thiolysate of procyanidin B2 was used as a standard. FIG. 9 shows the basic reaction of thiolytic cleavage. In thiolytic reaction, the PAC was reacted with benzylmercaptan under the acidic condition so that the extension units of PAC were released to the corresponding benzylthioether and the terminal units were released to free flavan-3-ols.

Figure 10:
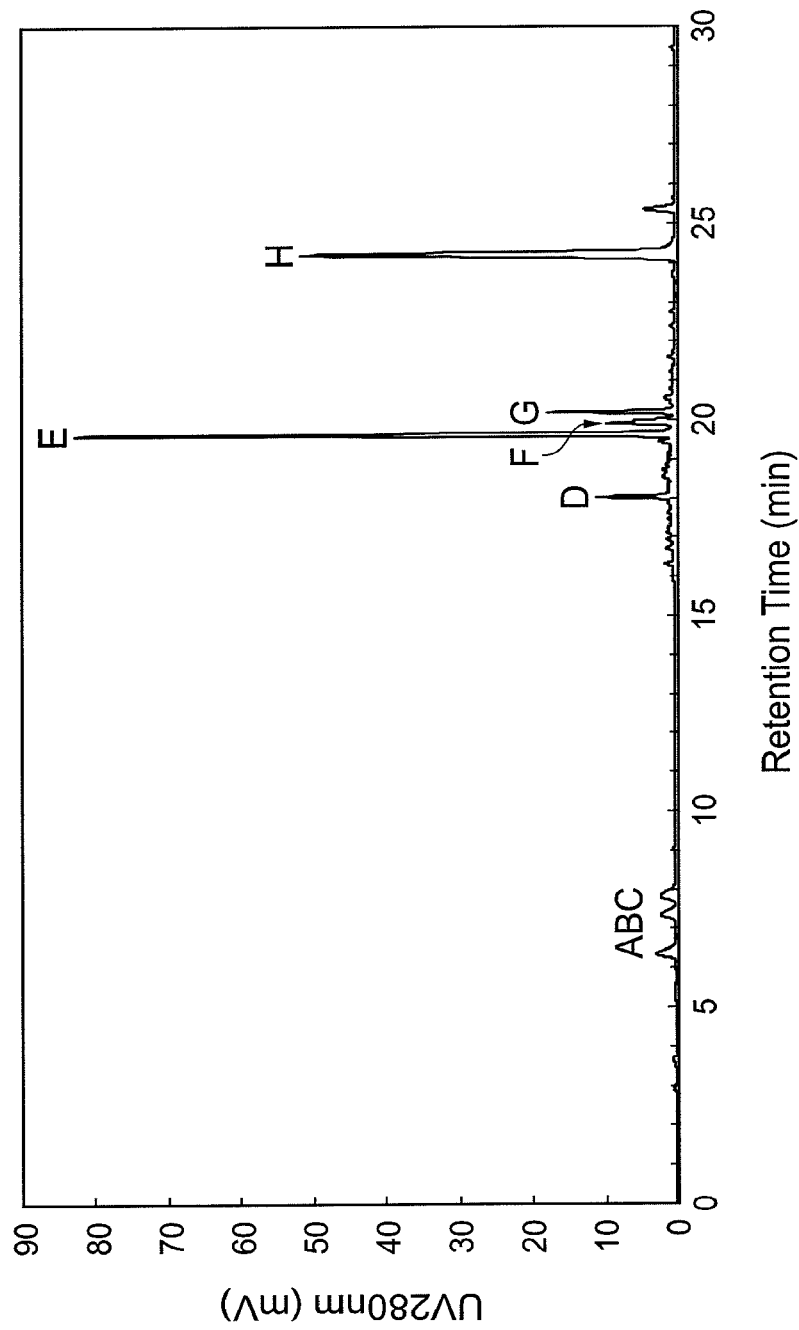
FIG. 10 shows reverse-phased HPLC chromatogram of thiolysate from LC3 (purified fraction from blueberry leaves).

As a result that thiolysis products of purified PAC in the LC3 fraction were analyzed in reverse-phased HPLC, several peaks were identified (FIG. 10). The peaks A, C and H were considered to be catechin, epicatechin and benzylmercaptan respectively according to the retention time of each standard preparation. Other peaks were confirmed by analyzing mass spectra.

The parent mass of peak E was [M-H]− at m/z 411.0892, with an estimated formula C22H20O6S (error=−3.8 ppm), and its MS/MS spectrum was [M-H]− at m/z 287.0510. The difference between the parental mass and MS/MS was 124.0382, which corresponded to a benzylthio adduct. Thus, peak E appeared to be catechin or epicatechin benzylthioether. Furthermore, when procyanidin B2 which is dimer consisting of only epicatechin was thiolysed, epicatechin and epicatechin benzylthioether as thiolysate were detected from the reaction mixture. Since the retention time of epicatechin benzylthioether from procyanidin B2 was the same as that of peak E, it was considered that that peak E was epicatechin benzylthioether.

The parental mass of peak G was [M-H]− at m/z 697.1385 (predicted formula: C37H30O12S) and its MS/MS was [M-H]− at m/z 573.0987. Again, the difference therebetween was 124.0398 and likely represented the benzylthio adduct. Thus, peak G was estimated to be a benzylthioether of A-type dimer consisting of catechin and/or epicatechin.

According to Thompson et al. (Thompson et al., J. Chem. Soc. Perkin Trans. 1 (1972) 1387), the interflavan linkages in PAC were resistant to thiolysis. After thiolysis, they would be released as free A-type dimmers, if present in the terminal units or as the corresponding benzylthioether, if present in the extension units (Foo et al., J. Nat. Prod. 63 (2000) 1225).

Peak B was detected as parent MS [M-H]− at m/z 863.1822 with a predicted formula C45H36O18 (error=−0.86 ppm). As the formula of B-type procyanidin trimer is C45H38O18 and that of A-type is C45H34O18, this peak was likely a trimer in which A-type and B-type interflavan bonds co-existed.

Peak D was detected as parent MS [M-H]− at m/z 985.2009 and a predicted formula was removed from benzylthio adduct to C45H36O18. Peak D was suggested to be an A-B type trimer similar to peak B but with a benzylthio adduct.

The parental mass of peak F was [M-H]− at m/z 605.1449 and its MS/MS was [M-H]− at m/z 481.1109, so that a benzylthio adduct was also present in peak F. However, the predicted formula could not be obtained from the parental mass. Since the predicted formula of peak F was undefined, peak F is indicated as "unknown" in TABLE 3.

The thiolysates of PAC from blueberry leaves were obtained free AB-type trimer, benzylthio adducts of AB-type trimer and A-type dimer other than flavan-3-ol monomer and flavan-3-ol benzylthioether. Since the constitution ratio of flavan-3-ol oligomer and their benzylthio adducts were high relatively, a calculating formula of mDP was modified.

The mean degree of polymerization (mDP) was calculated by the formula, mDP=[sum of (benzylthio adducts×n)+sum of (free flavan-3-ol×n)]/[total free flavan-3-ol], which "n" is DP of detected flavan-3-ol by thiolysis. Moreover, peak area of detected flavan-3-ol benzylthio adducts were corrected from thiolysates of procyanidin B2 preparation.

The structural analysis of HCV inhibitor PAC from blueberry leaves (LC3) is summarized in TABLE 3. The mDP of PAC in this fraction was estimated to be 7.7. The PAC from LC3 fraction was composed of primarily epicatechin, which was 65.1% and 58.1% in terminal units and extension respectively. In addition, the monomer composition of the A-type dimer and the AB-type trimer were unknown. Therefore, when flavan-3-ol monomer proportion was re-calculated only in detected monomers, 95% of the PAC from LC3 was composed of epicatechin.

TABLE 3

Thiolysis Results of Purified Fraction (LC3) from Blueberry Leaves

| | | Terminal (%) | | | | Extension (%) | | | | |
|---|---|---|---|---|---|---|---|---|---|---|
| | mDP | C | EC | AB-3 | Total | C | EC | A-2 | Unknown | AB-3 | Total |
| LC3 | 7.7 | 20.4 | 65.1 | 14.5 | 100 | 0.8 | 58.1 | 11.9 | 23.2 | 6.0 | 100 |

Notes:
c; catechin,
EC; epicatechin,
AB-3; trimer consisting of both A-type and B-type interflavan bonds,
A-2; A-type dimer.

Example 2

Extraction of PAC Contained in Some of Material and Replication Suppressive Activities 1. PAC Preparation from Various Materials From results of example 1, the proanthocyanidin (PAC) was identified as compound possessing the suppression activity of HCV replication. PAC is previously known as condensed tannin and contained in various plants and foods. It has been already reported that the following materials contain PAC, so, PAC fraction can be separated from these materials.

Sample 1; blueberry leaves
Sample 2; blueberry fruit
Sample 3; taro peel

Sample 4; pine bark extract (pycnogenol™)
Sample 5; grape seed extract (gravinol™)
Sample 6; apple polyphenol (applephenol™)
Sample 7; cranberry (cranberry powder)
Sample 8; strawberry fruit
Sample 9; peanut peel
Sample 10; croton sap (Sangre de Drago, Raintree Nutrition Inc.)

(Separation of PAC Fraction from Blueberry Leaves: Sample 1)

10 g of the lyophilized powder of rabbit-eye blueberry (*Vaccinium virgatum* Ayton) leaves was extracted with 100 ml of hexane for 30 min and the supernatant therefrom was decanted. This procedure was repeated three times, followed by washing in 100 ml of ethyl acetate for 30 min three times. The remaining residues were extracted with 100 ml of methanol for 30 min, and its supernatant was decanted and filtered. This procedure was repeated four times and the resulting crude methanol extracts were concentrated by rotary evaporator at 50° C. and lyophilized, finally resulting in approximately 3.5 g of solid powder.

The crude methanol extract (approx. 500 mg) was then dissolved in 60% methanol and placed on a Sephadex LH-20 column (50 mm×50 mm; GE Healthcare). In fractionation, the following series of solvents was used: 400 ml of 60% methanol; 400 ml of 100% methanol; 400 ml of 70% acetone. Each eluent were concentrated by evaporator and lyophilized, finally resulting in approximately 100 mg of solid PAC.

(Preparation of PAC Fraction from Sample 2~10)

Sample 2, 3 and 9 was prepared directly from raw material and Sample 4 to 8 and 10 was prepared from purchased materials containing PAC. All materials were extracted with 100% methanol, and concentrated by evaporator and lyophilized. Then each PAC preparations were processed by the same method aforementioned using Sephadex LH-20.

2. Composition Analysis of PAC Preparations

PAC samples prepared from each origin were analyzed by Porter method and thiolysis. Replicon cells were assayed for replication suppressive activity. These results are summarized as TABLE 4-6.

Table 6 shows the HCV replication suppressive activity, PAC contents and the compositions of propelargonidin (PP), procyanidin (PC) and prodelphinidin (PD) which were calculated from results of thiolysis. In the samples showing no PAC contents value of table 6, there were detected little quantity of the yielding PAC.

The mDP value of PAC preparations from blueberries (Sample 1 or 2) was around 12 and their composition had epicatechin-rich structure and A-type of interflavan bond. The mDP of PAC from taro peel (Sample 3) was 10.5 and the most of them were epicatechin and possessed A-type bond. In pycnogenol, mDP was approximately 6.5, and epicatechin was high in composition ratio of extension units, but it was high catechin in that of terminal units.

The gravinol (Sample 5) was characterized by that the mDP value had relatively-long about 14.4, and the composition ratio of epicatechin-gallate was high in comparison with others. The mDP value of the applephenon (Sample 6) was approx. 4.4, same long as that of strawberry (Sample 8). Moreover, both samples (Sample 6 and 8) possessed high ratio of epicatechin composition, but epiafzelechin content was approximately 10% detected only in the strawberry (sample 8). The mDP of the cranberry fruit (Sample 7) and the peanut peel (Sample 9) were 6.6 and 7.4 respectively, and both samples had comparatively high ratio of A-type interflavan bond. The croton sap (Sample 10) was characterized in that the mDP value was 8.3 and the composition ratio of epicatechin was high, but gallocatechin and epigallocatechin were detected only in the PAC from the croton sap (sample 10), and the ratio became to 37.4% when gallocatechins were converted into prodelphinidin.

In HCV replication suppressive activities, the IC50 value of sample 1 to 9 were less than 1.0 μg/ml, and the ratio was more than 10. It leads to the conclusion in which these samples could be evaluated to have the suppressive activity on HCV replication. But, in case of the croton sap (sample 10), the IC50 was more than 1.0 μg/ml, and the ratio of that was less than 10, so that this was evaluated to have no activity.

From these results, almost all PAC from various plant origins were identified to have HCV replication suppressive activity in replicon cells, except PAC containing much prodelphinidin (PD) composition ratios such as croton sap (sample 10), because it could not be confirmed to has the suppressive activity.

TABLE 4

The mDP and Composition of PAC Preparations by Thiolysis

| | | Terminal Units | | | | | | | |
|---|---|---|---|---|---|---|---|---|---|
| | mDP | Af (%) | EAf (%) | C (%) | EC (%) | GC (%) | EGC (%) | A-2 (%) | AB-3 (%) | Total |
| Blueberry Leaf | 11.2 | — | — | 31.2 | 42.6 | — | — | — | 26.2 | 100 |
| Blueberry Fruit | 12.6 | — | — | 43.6 | 56.4 | — | — | — | — | 100 |
| Taro Peel | 10.5 | — | — | — | 100.0 | — | — | — | — | 100 |
| Pycnogenol | 6.5 | — | — | 96.4 | 3.6 | — | — | — | — | 100 |
| Gravinol | 14.4 | — | — | 61.7 | 38.3 | — | — | — | — | 100 |
| Applephenon | 4.4 | — | — | 10.7 | 89.3 | — | — | — | — | 100 |
| Cranberry Fruit | 6.6 | — | — | — | 41.8 | — | — | 58.2 | — | 100 |
| Strawberry Fruit | 4.4 | — | 25.5 | 33.4 | 41.0 | — | — | — | — | 100 |
| Peanuts Peel | 7.4 | — | — | 8.7 | 8.9 | — | — | 77.0 | 5.4 | 100 |
| Croton Sap | 8.3 | — | — | — | 36.0 | 4.5 | 59.5 | — | — | 100 |

TABLE 5

The mDP and Composition of PAC Preparations by Thiolysis

| | Af (%) | EAf (%) | C (%) | EC (%) | GC (%) | EGC (%) | Cg (%) | ECg (%) | Unknown (%) | A-2 (%) | AB-3 (%) | Total |
|---|---|---|---|---|---|---|---|---|---|---|---|---|
| Blueberry Leaf | — | — | — | 69.6 | — | — | — | — | 8.2 | 13.3 | 8.9 | 100 |
| Blueberry Fruit | — | — | — | 85.6 | — | — | — | — | 3.7 | 6.2 | 4.6 | 100 |
| Taro Peel | — | — | — | 90.8 | — | — | — | — | — | 8.2 | 1.0 | 100 |
| Pycnogenol | — | — | 16.9 | 83.1 | — | — | — | — | — | — | — | 100 |
| Gravinol | — | — | 8.7 | 41.7 | — | — | 2.8 | 46.8 | — | — | — | 100 |
| Applephenon | — | — | 3.5 | 94.1 | — | — | — | 2.4 | — | — | — | 100 |
| Cranberry Fruit | — | — | 1.4 | 68.5 | — | — | — | — | — | 19.5 | 10.5 | 100 |
| Strawberry Fruit | 0.7 | 4.9 | 19.0 | 75.4 | — | — | — | — | — | — | — | 100 |
| Peanuts Peel | — | — | 7.3 | 44.4 | — | — | — | — | — | 24.7 | 23.6 | 100 |
| Croton Sap | — | 2.7 | 12.4 | 51.1 | 16.8 | 16.9 | — | — | — | — | — | 100 |

Af; afzelechin, EAf; epiafzelechin, C; catechin, EC; epicatechin, GC; gallocatechins, EGC; Epigallocatechin, Cg; catechin-gallate, ECg; epicatechin-gallate, A-2; A-type dimer, AB-3; trimer consisting of both A-type and B-type interflavan bond.

TABLE 6

Anthocyanidin Components and Replicon Assay of PAC Preparations

| | Composition | | | Replicon Assay | | | PAC |
|---|---|---|---|---|---|---|---|
| | PP (%) | PC (%) | PD (%) | IC50 (μg/ml) | CC50 (μg/ml) | Ratio | Content (%) |
| Blueberry Leaf | — | 100.0 | — | 0.56 | 16.26 | 29.0 | 88.1 |
| Blueberry Fruit | — | 100.0 | — | 0.25 | 15.03 | 60.1 | — |
| Taro Peel | — | 100.0 | — | 0.18 | 13.24 | 73.6 | 80.6 |
| Pycnogenol | — | 100.0 | — | 0.56 | 18.88 | 33.7 | 65.0 |
| Gravinol | — | 100.0 | — | 0.20 | 9.95 | 49.8 | 55.9 |
| Applephenon | — | 100.0 | — | 0.61 | 22.26 | 36.5 | 60.6 |
| Cranberry Fruit | — | 100.0 | — | 0.31 | 15.95 | 51.5 | — |
| Strawberry Fruit | 10.2 | 89.8 | — | 0.20 | 11.70 | 58.5 | 52.1 |
| Peanuts Peel | — | 100.0 | — | 0.11 | 9.01 | 81.9 | 96.8 |
| Croton Sap | 2.4 | 60.2 | 37.4 | 5.89 | 23.62 | 4.0 | 64.9 |

PP; propelargonidin,
PC; procyanidin,
PD; prodelphinidin

Example 3

The Bulk Preparation of PAC from Blueberry Leaves

To prepare PAC from blueberry leaves, freeze-dried powder (105 g) was extracted with 1.2 liters of acetone for 10 min and the supernatant obtained was then decanted. This procedure was repeated five times to remove the green pigment from the leaves, followed by washing in 1.2 liters of hexane for 10 min. The remaining residues were washed with ethyl acetate. The washed powder of leaves was further extracted with 1.2 liters of methanol for 30 min, and the supernatant obtained was then filtered. This procedure was repeated four times and the resulting crude methanol extracts were concentrated by rotary evaporator at 50° C. and lyophilized, finally resulting in approximately 30 g of solid powder.

The crude methanol extract (15 g) was then dissolved in 1.0 liters of 60% methanol and placed on a Sephadex LH-20 column (50 mm×920 mm; GE Healthcare). Fractionation was performed using the following series of solvents: fraction I, 9.0 L of 60% methanol (retrieved weight: 10.2 g); fraction II, 9.0 L of 100% methanol (retrieved weight: 3.3 g); fraction III, 9.0 L of 70% acetone (retrieved weight: 1.3 g). In each fraction, the eluate was divided into 28 sub-fractions per liter.

After fractionation on a Sephadex LH-20 column, each eluate was thiolysed to determine the components and mDP of PAC (FIG. 11). Then, PAC with different mDP from blueberry leaves was assessed for the inhibitory activity of HCV replication. The HCV replication suppressive activity of PAC from blueberry leaves was clearly dependent on polymerization degree level and the apex activity was observed at a polymerization degree level of around 8 to 9. In this illustrative embodiment, mDP of PAC was preferably at least 5.

(Discussion)

In FIG. 4 to 6, when the prodelphinidin units ($R_1=R_2=R_3=OH$) is high in PAC composition, the IC50 value of Sample 10 is more than 1.0 μg/ml and the ratio is less than 10, so that it is not able to use as anti-HCV agent. In PAC composition of this invention, the degree of polymerization is more than or equal to 3, and delphinidin content was low, so that HCV replication inhibition activity became strong, namely it is useful as anti-HCV agent.

Industrial Applicability

The HCV production suppressant of this invention possesses the superior anti-HCV effect, so that it is applied to therapeutic medicine or dietary supplements of hepatic disorders from HCV, instead of the interferon therapy.

What is claimed is:

1. A method for producing a composition for inhibiting production of hepatitis C virus (HCV), comprising:
preparing a proanthocyanidin composition
having an anti-HCV production activity value (IC50) which is:
less than 0.61 μg/ml, and
less than or equal to one tenth of the concentration of the proanthocyanidin composition for inhibiting 50% of cell proliferation (CC50); and
comprising a proanthocyanidin having 5 to 10 monomer units, each of which consists of the flavan-3-ol illustrated in the general formula (1):

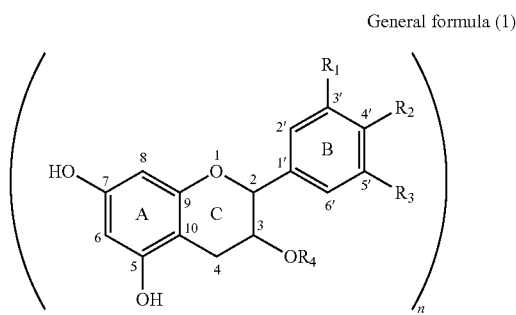

General formula (1)

wherein $R_1$ is hydrogen, $R_2$ is hydroxyl, $R_3$ is hydrogen or hydroxyl, $R_4$ is hydrogen or a gallate group, and n is 5-10;

said units of flavan-3-ol being bonded to each other in any one of three bond patterns as follows:

(i) the bond between carbon at position 4 and carbon at position 8, (ii) the bond between carbon at position 4 and carbon at position 6, (iii) the bond between carbon at position 4 and carbon at position 8, and between carbon at position 2 and oxygen at position 7; and forming the composition for inhibiting production of HCV comprising the proanthocyanidin composition.

2. The method according to claim 1, wherein the proanthocyanidin composition is prepared from an extract of blueberry leaves.

3. The method according to claim 1, wherein the mean polymerization degree of the proanthocyanidin is 5 to 9.

4. A method for inhibiting production of HCV comprising: administering a composition prepared by the method according to claim 1 to a patient in need thereof.

5. The method according to claim 4, wherein the proanthocyanidin composition is prepared from an extract of blueberry leaves.

6. The method according to claim 4, wherein the mean polymerization degree of the proanthocyanidin is 5 to 9.

* * * * *